US009290806B2

(12) United States Patent
Stolovitzky et al.

(10) Patent No.: US 9,290,806 B2
(45) Date of Patent: Mar. 22, 2016

(54) FABRICATING SELF-FORMED NANOMETER PORE ARRAY AT WAFER SCALE FOR DNA SEQUENCING

(71) Applicant: International Business Machines Corporation, Armonk, NY (US)

(72) Inventors: Gustavo A. Stolovitzky, Riverdale, NY (US); Deqiang Wang, Ossining, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 14/608,675

(22) Filed: Jan. 29, 2015

(65) Prior Publication Data
US 2015/0141299 A1    May 21, 2015

Related U.S. Application Data

(63) Continuation of application No. 13/469,220, filed on May 11, 2012, now Pat. No. 8,986,980.

(51) Int. Cl.
| C12Q 1/68 | (2006.01) |
| B82Y 15/00 | (2011.01) |
| B82Y 40/00 | (2011.01) |
| B81C 1/00 | (2006.01) |
| B82Y 5/00 | (2011.01) |

(52) U.S. Cl.
CPC .......... *C12Q 1/6874* (2013.01); *B81C 1/00087* (2013.01); *B82Y 15/00* (2013.01); *B82Y 40/00* (2013.01); *C12Q 1/6869* (2013.01); *B82Y 5/00* (2013.01); *Y10S 977/723* (2013.01); *Y10S 977/74* (2013.01); *Y10S 977/742* (2013.01); *Y10S 977/781* (2013.01); *Y10S 977/904* (2013.01); *Y10S 977/92* (2013.01); *Y10S 977/953* (2013.01); *Y10S 977/958* (2013.01)

(58) Field of Classification Search
CPC .... G01N 27/3278; B81B 1/002; B81B 1/004; C12Q 1/6825; C12Q 1/6834; C12Q 1/6869
See application file for complete search history.

(56) References Cited

U.S. PATENT DOCUMENTS

| 6,503,409 B1 | 1/2003 | Fleming |
| 7,005,264 B2 | 2/2006 | Su et al. |
| 7,077,939 B1 | 7/2006 | Crooks et al. |
| 7,678,562 B2 | 3/2010 | Ling |
| 2009/0321355 A1 | 12/2009 | Ratto et al. |
| 2010/0233781 A1 | 9/2010 | Bangera et al. |
| 2011/0120868 A1 | 5/2011 | Lindsay et al. |

(Continued)

OTHER PUBLICATIONS

A. J. Storm et al., "Fabrication of Solid-State Nanopores with Single-Nanometre Precision," Nature Materials, vol. 2, 2003, 537-540.

(Continued)

*Primary Examiner* — J. Christopher Ball
(74) *Attorney, Agent, or Firm* — Cantor Colburn LLP

(57) ABSTRACT

A technique is provided for a structure. A substrate has a nanopillar vertically positioned on the substrate. A bottom layer is formed beneath the substrate. A top layer is formed on top of the substrate and on top of the nanopillar, and a cover layer covers the top layer and the nanopillar. A window is formed through the bottom layer and formed through the substrate, and the window ends at the top layer. A nanopore is formed through the top layer by removing the cover layer and the nanopillar.

14 Claims, 26 Drawing Sheets

(56) References Cited

U.S. PATENT DOCUMENTS

2011/0279125 A1    11/2011    Bedell et al.
2012/0118739 A1    5/2012    Walavalkar et al.

OTHER PUBLICATIONS

B. C. Gierhart et al., "Nanopore with Transverse Nanoelectrodes for Electrical Characterization and Sequencing of DNA," Sensors and Actuators B: Chemical, vol. 132, Issue 2, Jun. 16, 2008, pp. 593-600.

Binquan Luan, et al., "Base-by-Base Ratcheting of Single Stranded DNA through a Solid-State Nanopore," NIH Public Access, published in final edited form as: "Phys Rev Lett. Jun. 11, 2010; 104(23): 238103," 9 pages.

C. Dekker, "Solid-State Nanopores," Nature Nanotechnology, vol. 2, 2007, pp. 209-215.

D. Branton, et al 2008, "The Potential and Challenges of Nanopore Sequencing," Digital Access to Scholarship at Harvard, Nature Biotechnology 26(10): 1146-1153; published version: doi:10.1038/nbt.1495; Accessed: Nov. 24, 2010, Internet: http://nrs.harvard.edu/urn-3:HUL.InstRepos:2664284; pp. 1-19.

G. M. King et al., "Probing Nanotube-Nanopore Interactions," Phys. Rev. Lett., vol. 95, 2005, 216103, 4 pages.

Jiali Li, et al, "Ion-beam Sculpting at Nanometre Length Scales," 2001 Macmillan Magazines Ltd., Nature, vol. 412, Jul. 12, 2001, www.nature.com, 4 pages.

Jijin Yang, et al., "Rapid and Precise Scanning Helium lion Microscope Milling of Solid-state Nanopores for Biomolecule Detection," IOP Publishing, Nanotechnology 22 (2011) 285310 (6 pp); Internet: stacks.iop.org/Nano/22/285310.

R. M. M. Smeets, et al., "Low-frequency Noise in Solid-state Nanopores," Internet: stacks.iop.org/Nano/20/095501; IOP Publishing; Nanotechnology 20 (2009) 095501 (4 pp).

U.S. Appl. No. 13/092,424; Titled: Self-Sealed Fluidic Channels for a Nanopore Array; filed Apr. 22, 2011; Inventors: B. Dang et al.

U.S. Appl. No. 13/228,491; Titled: Embedding a Nanotube Inside a Nanopore for DNA Translocation; filed Sep. 9, 2011; Inventors: A. Afzali-Ardakani et al.

W. Timp et al, "Nanopore Sequencing: Electrical Measurements of the Code of Life," IEEE Transactions on Nanotechnology, vol. 9, No. 3, May 2010, pp. 281-294.

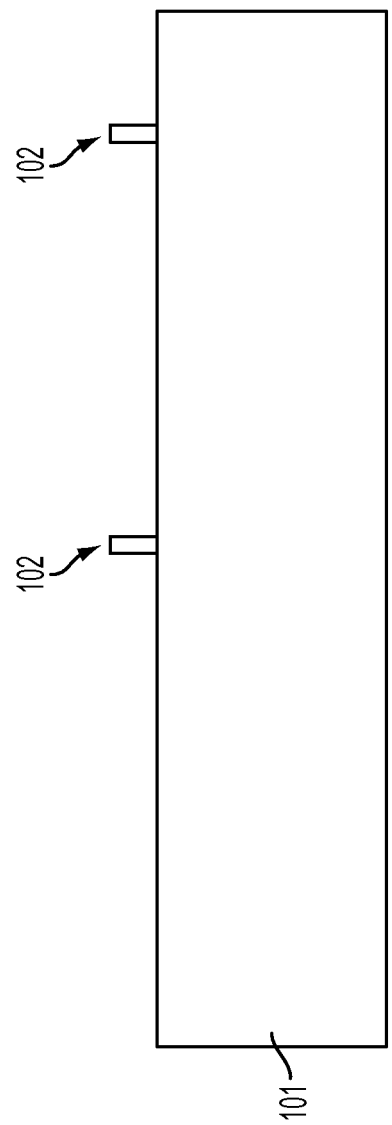

FABRICATING SELF-FORMED NANOMETER PORE ARRAY AT WAFER SCALE FOR DNA SEQUENCING

DOMESTIC PRIORITY

This is a continuation application of U.S. non-provisional application Ser. No. 13/469,220 filed May 11, 2012, the contents of which are incorporated by reference herein.

BACKGROUND

The present invention relates generally to fabricating a self-formed nanometer pore, and more specifically, to forming a self-formed nanometer pore array at the wafer scale.

A solid state nanopore is a nanometer pore on a freestanding single or multi-layer membrane, like silicon nitride, silicon dioxide, and titanium nitride/silicon dioxide stack. The solid state nanopore is being widely used to detect individual characteristics of deoxyribonucleic acid (DNA), ribonucleic acid (RNA), and protein at single molecule scale, and is very promising technology for next-generation personal genome sequencing.

Nanopore sequencing is a method for determining the order in which nucleotides occur on a strand of deoxyribonucleic acid (DNA). A nanopore (also referred to as a pore, nanochannel, hole, etc.) can be a small hole in the order of several nanometers in internal diameter. The theory behind nanopore sequencing is about what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

SUMMARY

According to an embodiment, a structure is provided. The structure includes a substrate having a nanopillar vertically positioned on the substrate and a bottom layer formed beneath the substrate. A top layer is formed on top of the substrate and on top of the nanopillar, and a cover layer covers the top layer and the nanopillar. A window is formed through the bottom layer and formed through the substrate, and the window ends at the top layer. A nanopore is formed through the top layer by removing the cover layer and the nanopillar.

According to an embodiment, a structure is provided. The structure includes a substrate having a nanopillar vertically positioned on the substrate, and a bottom layer formed beneath the substrate. Top layers are formed on top of the substrate and on top of the nanopillar, and a cover layer covers the top layers and the nanopillar. A window is formed through the bottom layer and formed through the substrate, and the window ends at the top layers. A nanopore is formed through the top layers by removing the cover layer and the nanopillar.

According to an embodiment, a structure is provided. The structure includes a substrate having a top layer and a bottom layer, and a hole formed through the top layer. The hole is coated with a coating to capture a carbon nanotube in the hole, and the captured carbon nanotube is positioned in the hole. A window is formed through the bottom layer and formed through the substrate, and the window ends at the top layer. A cover layer covers the top layer and the carbon nanotube positioned in the hole. A nanopore is formed through the cover layer by removing the carbon nanotube from the cover layer.

According to an embodiment, a structure is provided. The structure includes a substrate having top layers and a bottom layer, and a hole formed through the top layers. The hole is coated with a coating to capture a carbon nanotube in the hole, and the capture carbon nanotube is positioned in the hole. A window is formed through the bottom layer and formed through the substrate, and the window ends at the top layers. A cover layer covers the top layers and the carbon nanotube positioned in the hole. A nanopore is formed through the cover layer by removing the carbon nanotube from the cover layer.

According to an embodiment, a method is provided for configuring a structure. The method includes vertically positioning a nanopillar on a substrate, forming a bottom layer beneath the substrate, and forming a top layer on top of the substrate and on top of the nanopillar. A cover layer covers the top layer and the nanopillar. The method includes forming a window through the bottom layer and through the substrate, where the window ends at the top layer. The method includes forming a nanopore through the top layer by removing the cover layer and the nanopillar.

According to an embodiment, a method for configuring a structure provided. The method includes vertically positioning a nanopillar on a substrate, forming a bottom layer beneath the substrate, and forming top layers on top of the substrate and on top of the nanopillar. A cover layer covers the top layers and the nanopillar. The method includes forming a window through the bottom layer and through the substrate, where the window ends at the top layers. The method includes forming a nanopore through the top layers by removing the cover layer and the nanopillar.

According to an embodiment, a method for configuring a structure is provided. The method includes forming a top layer and a bottom layer on a substrate, and forming a window through the bottom layer and through the substrate, where the window ends at the top layer. The method includes forming a hole through the top layer. The hole is coated with a coating to capture a carbon nanotube in the hole, and the carbon nanotube is captured to be positioned in the hole. The method includes forming a cover layer to cover the top layer and the carbon nanotube positioned in the hole, and forming a nanopore through the cover layer by removing the carbon nanotube from the cover layer.

According to an embodiment, a method for configuring a structure is provided. The method includes forming a top lay and a bottom layer on a substrate, and forming a window through the bottom layer and through the substrate, where the window ends at the top layer. The method includes forming a hole through the top layers, where the hole is coated with a coating to capture a carbon nanotube in the hole. The carbon nanotube is captured to be positioned in the hole. The method includes forming cover layers to cover the top layer and the carbon nanotube positioned in the hole, and forming a nanopore through the cover layers by removing the carbon nanotube from the cover layers.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 1A illustrates a cross-sectional view of a structure during the processes to fabricate a single self-formed nanometer pore and/or an array of self-formed nanometer pores according to an embodiment.

DETAILED DESCRIPTION

Currently, transmission electron microscope and ion sputtering systems are widely used for making a nanometer pore. Other methods are also employed, such as focused ion beam, scanning helium ion microscope (HIM), etc. Those tools and methods can make sub-nanometer nanopores, but the efficiency is very low. The productivity of making many nanopores does not improve much, while the cost is very high. For example, these tools and methods cannot be used to make a nanopore array at the wafer scale. For this reason, in order to meet the requirements of electron beam (E-beam) lithography or HIM technology, the (silicon or other type of) wafer (e.g., around 200 mm in diameter) must be diced into single chips (e.g., 10 mm by 10 mm in size). Then, E-beam or HIM can make one nanopore in the 10 mm by 10 mm single chip. The efficiency and productivity of this process is low.

However, to make nanopores with a high-throughput (i.e., increased productivity) and in a low cost manner, embodiments disclosed herein provide techniques to make a nanometer pore array at wafer scale. For example, embodiments provide mechanisms to process/form the nanopores (directly) on the wafer before dicing the wafer into single chips.

Embodiments herein provide techniques to fabricate a self-formed nanometer pore array at water scale for DNA sequencing or other applications. A solid state nanopore is a nanometer pore on a free-standing single or multi-layer membrane, such as, e.g., silicon nitride, silicon dioxide, and titanium nitride/silicon dioxide stack. This can be used to detect individual characteristics of DNA, RNA, and protein at single molecule scale.

Figure 1B:
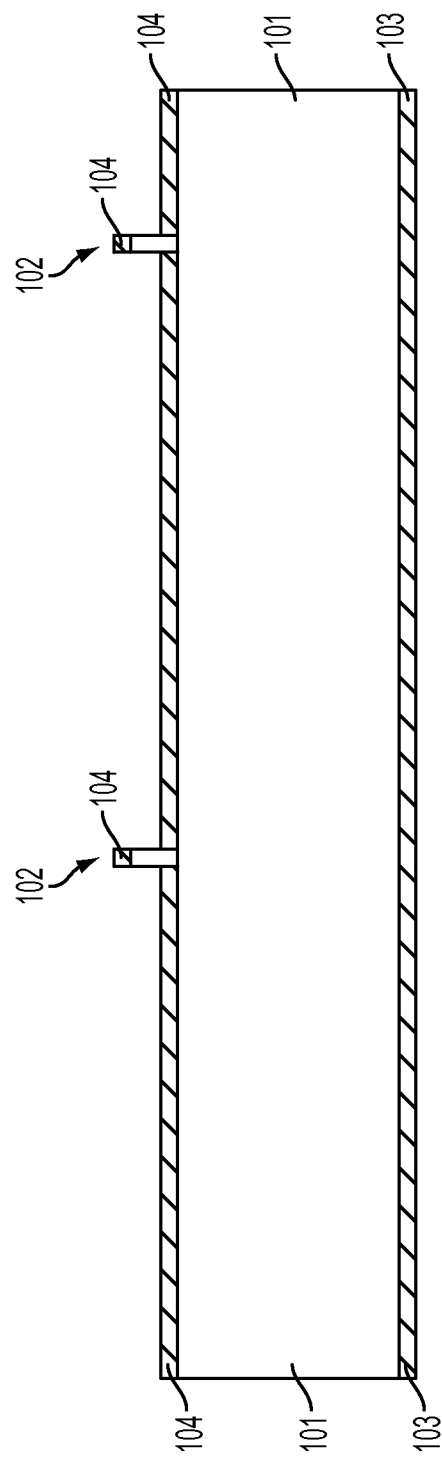
FIG. 1B illustrates a cross-sectional view of the structure during the processes to fabricate a single self-formed nanometer pore and/or an array of self-formed nanometer pores according to an embodiment.

Now turning to the figures, FIGS. 1A, 1B, 1C, 1D, 1E, and 1F illustrate the processes to fabricate the structure for a single self-formed nanometer pore and/or an array of self-formed nanometer pores for DNA sequencing according to an embodiment. FIGS. 1A, 1B, 1C, 1D, 1E, and 1F each depict a cross-sectional schematic of the structure during the processes to fabricate the self-formed nanometer pore. In FIG. 1A, substrate 101 (wafer) is any electrically insulating substrate (like silicon). Nanopillar 102 is a standing pillar of any nanometer size in diameter. The nanopillar 102 can be any material, such as silicon, silicon dioxide, carbon nanotube, etc. The diameter (size) of the nanopillar 102 can be any range from nanometer to micrometer, or even larger if so desired. The diameter of the nanopillar 102 will determine the size (diameter) of nanopore 108 shown in FIG. 1F.

The nanopillar 102 can be fabricated through standard semiconductor processes or other methods as understood by one skilled in the art. For example, for silicon, different diameters for the nanopore 108 can be achieved by different reactive ion etch or wet etch times for the nanopillar 102. The height of the nanopillar 102 will determine the maximum thickness of the nanopore 108. For a nanopillar 102 made of silicon dioxide, thermal oxidation methods can be used to silicon dioxide on the silicon substrate 101 (and multiple nanopillars 102 when forming an array of nanopillars) can be formed on the substrate 101 by etching as understood by one skilled in the art. In one case, silicon dioxide can be grown on the substrate 101, and a mask can be applied to etch away the silicon dioxide to leave the vertical standing nanopillar 102 of silicon dioxide as understood by one skilled in the art.

Figure 1C:
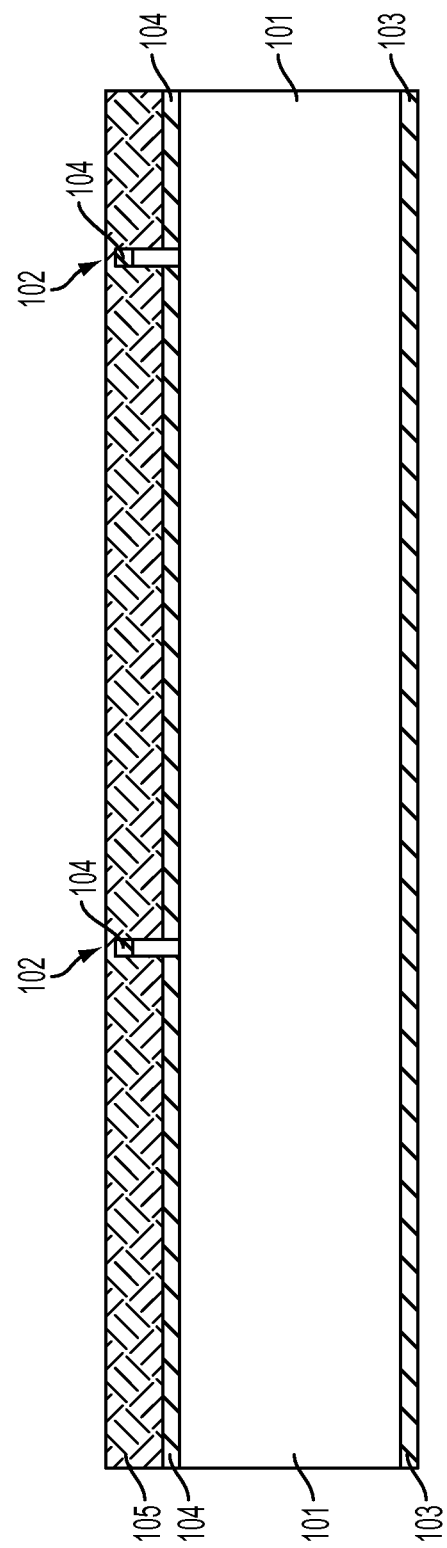
FIG. 1C illustrates a cross-sectional view of the structure during the processes to fabricate a single self-formed nanometer pore and/or an array of self-formed nanometer pores according to an embodiment.
Figure 1D:
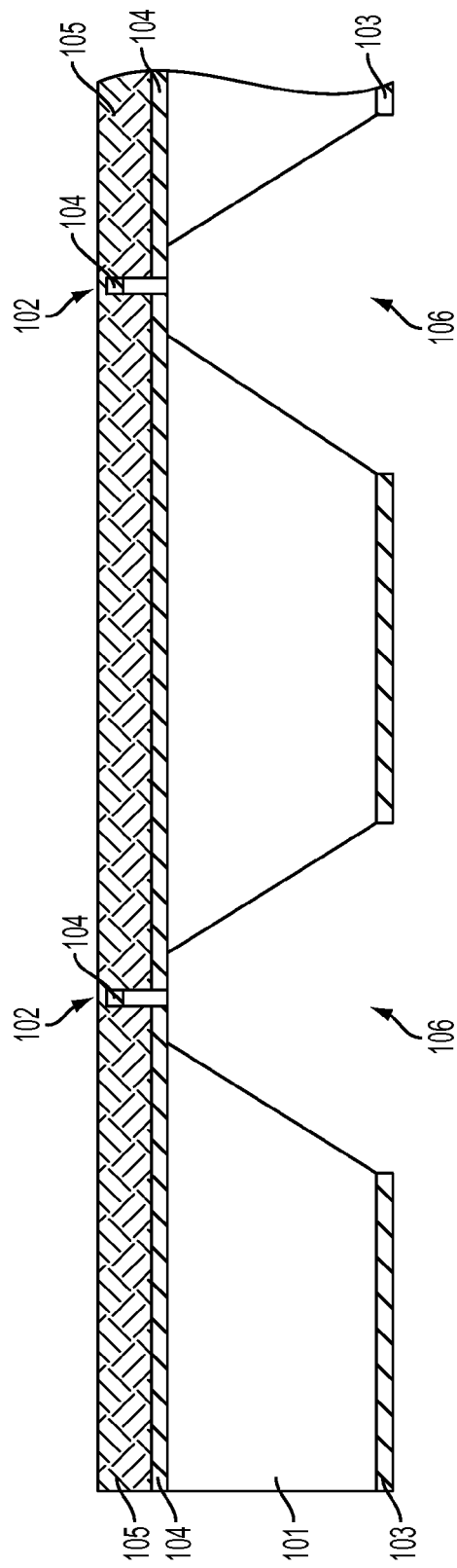
FIG. 1D illustrates a cross-sectional view of a structure during the processes to fabricate a single self-formed nanometer pore and/or an array of self-formed nanometer pores according to an embodiment.

In FIG. 1B, layers 103 and 104 are applied to the substrate 101, and the layers 103 and 104 can be electrically insulating films, such as silicon nitride. Layer 103 can be one type of insulating film, and layer 104 can be another type of insulating film. Layer 104 is also formed on top of the nanopillar 102. The nanopore 108 will form in layer 104 (as seen in FIG. 1F). The thickness of layer 104 is the (same) thickness (depth) of the nanopore 108. In FIG. 1C, layer 105 is applied to the top of layer 104 and the top of the nanopillar 102. Layer 105 is an electrically insulating film, like silicon dioxide. Layer 105 will (completely) protect the top surface of substrate 101 and the nanopillar 102 during subsequent etching. Layer 105 is thick enough to also cover the sides of the nanopillar 102, such that the entire nanopillar 102 is covered along with the small portion of layer 104 on top of the nanopillar 102.

Layer 103 will protect the bottom of the substrate 101. Layers 103 and 105 will be the etch mask to form the window 106 shown in FIG. 1D. Window 106 can be fabricated by standard semiconductor processes as understood by one skilled in the art, such as by wet or drying etching. The window 106 is formed through layer 103 and through the substrate 101. The window 106 ends at the bottom layer 104 and bottom of the nanopillar 102.

Figure 1E:
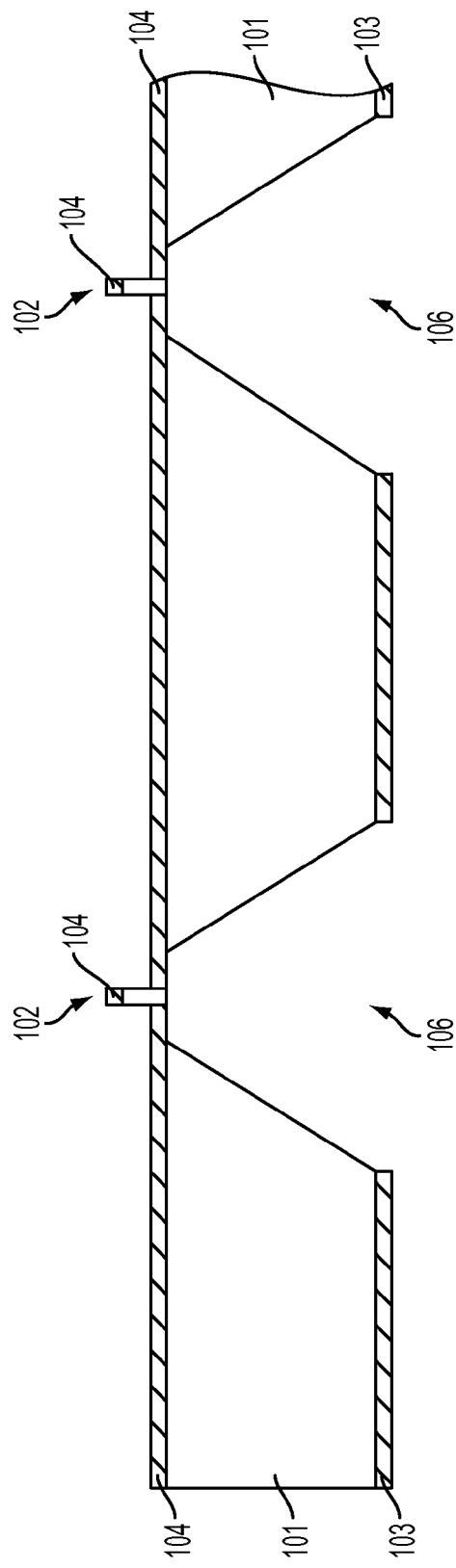
FIG. 1E illustrates a cross-sectional view of the structure during the processes to fabricate a single self-formed nanometer pore and/or an array of self-formed nanometer pores according to an embodiment.
Figure 1F:
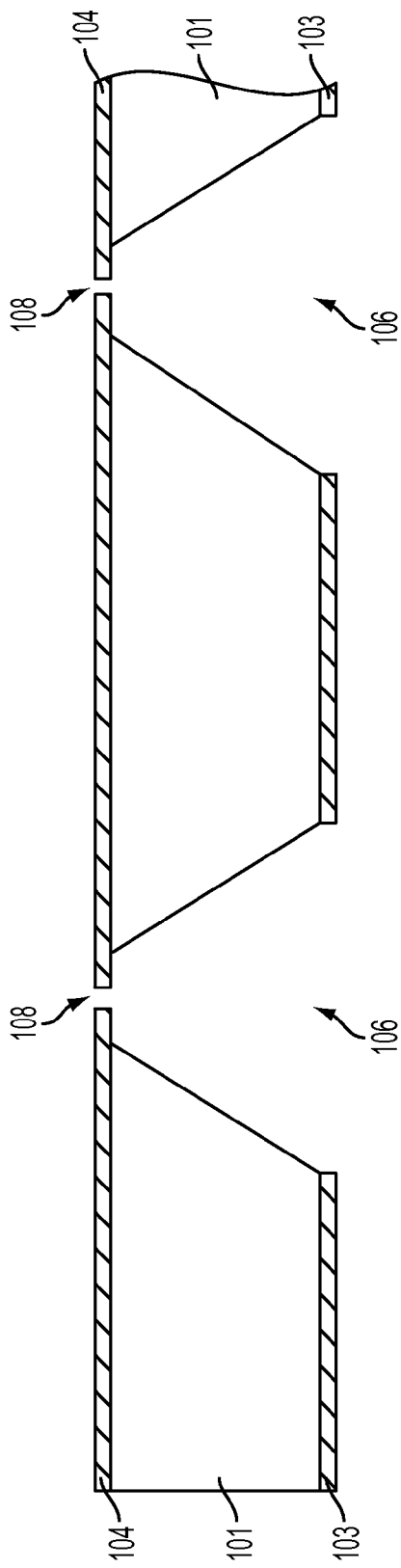
FIG. 1F illustrates a cross-sectional view of the structure during the processes to fabricate a single self-formed nanometer pore and/or an array of self-formed nanometer pores according to an embodiment.

In FIG. 1E, the layer 105 is removed selectively by dry or wet etching methods as understood by one skilled in the art. This leaves layer 104 and nanopillar 102 positioned/fixed in the layer 104.

In FIG. 1F, the nanopore 108 is formed by removing the nanopillar 102 with dry or wet etch processes. The nanopillar 102 can be removed by selective wet or dry etching methods. For example, tetramethylammonium hydroxide (TMAH) can be utilized to etch away the silicon nanopillar 102 as understood by one skilled in the art based on the teachings disclosed herein.

Figure 2A:
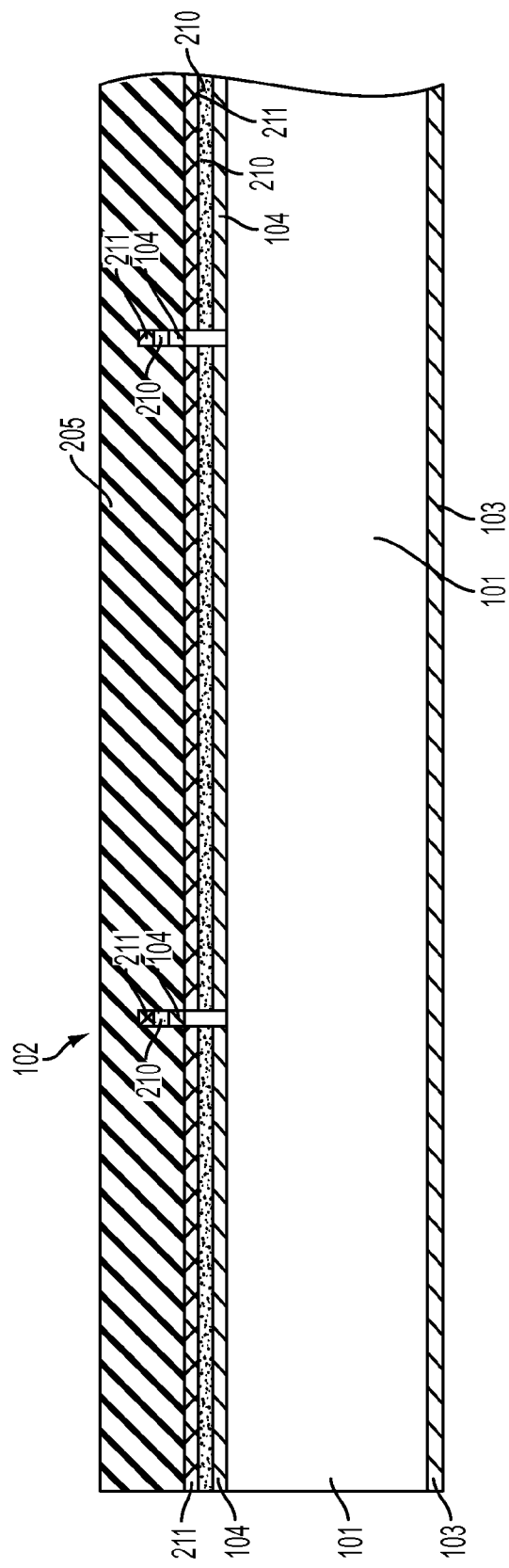
FIG. 2A illustrates further processes to form the structure for a multilayer nanopore according to an embodiment.
Figure 2B:
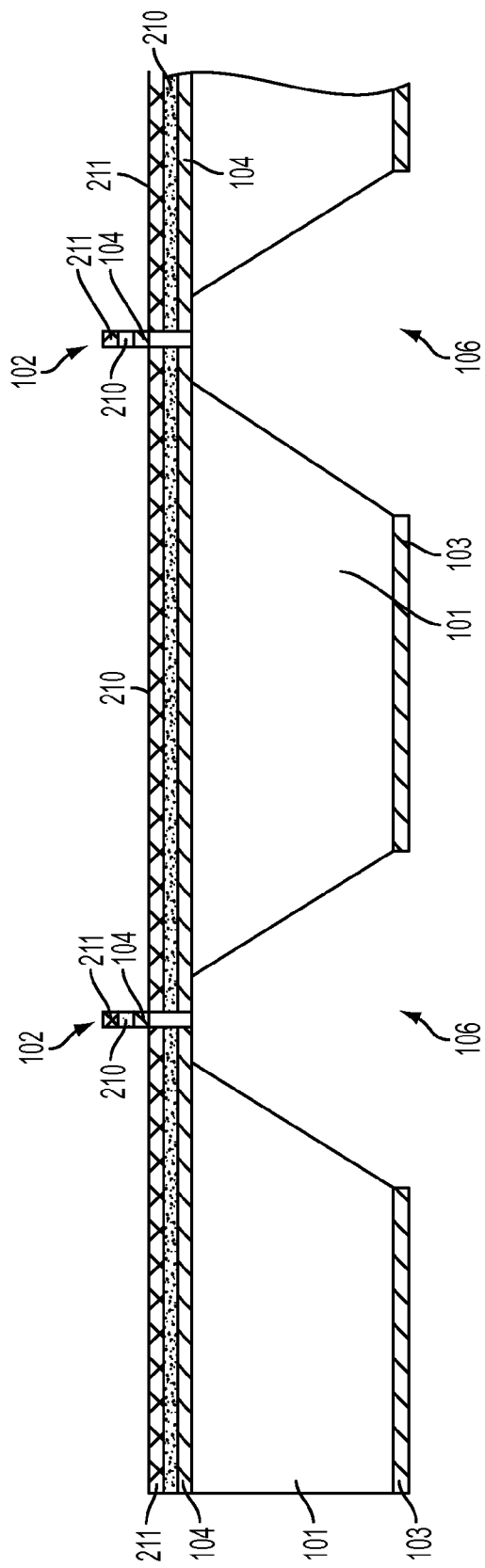
FIG. 2B illustrates further processes to form the structure for the multilayer nanopore according to an embodiment.
Figure 2C:
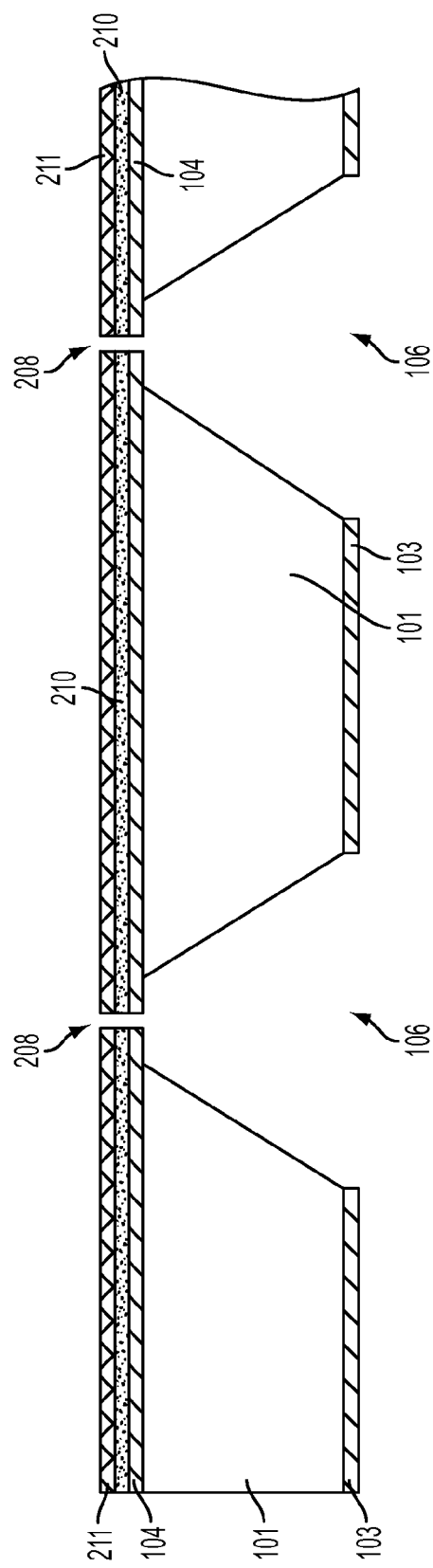
FIG. 2C illustrates further processes to form the structure for the multilayer nanopore according to an embodiment.

FIGS. 2A, 2B, and 2C illustrate further processes to form the structure for a multilayer nanopore according to an embodiment. FIGS. 2A, 2B, and 2C are collectively referred to as FIG. 2 and incorporate the processes discussed in FIG. 1. As such, the processes of FIGS. 1A and 1B will be briefly discussed first. For example, FIG. 2 includes the substrate 101 and nanopillar 102 shown in FIG. 1A. As discussed herein, the nanopillar 102 is any nanometer size standing pillar in diameter. The nanopillar 102 can be any material, such as silicon, silicon dioxide, carbon nanotube, etc. The diameter (size) of the nanopillar 102 can be any range from nanometer to micrometer, or even larger if so desired. The diameter of the nanopillar 102 will decide the size (diameter) of nanopore 208.

FIG. 2 also includes layer 103 formed on the bottom of the substrate 101 and layer 104 formed on the top of both the substrate 101 and nanopillar 102 as shown in FIG. 1B. Layers 103 and 104 are electrically insulating films, such as silicon nitride. In one case, layer 103 can be one type of insulating film, and layer 104 can be another type of insulating film.

Now referring to FIG. 2A, layer 210 is formed on top of layer 104 and the top of nanopillar 102. Layer 211 is formed on the top of layer 210 and the top of the nanopillar 102. The layers 210 and 211 can be any film, such as insulating and/or conductive films.

The layers 104, 210, and 211 are the multilayers utilized to form the thickness of the nanopore 208. As seen in FIG. 2A, the layers 104, 210, and 211 are (consecutively) stacked on top of the nanopillar 102 and surround the sides of the nanopillar 102. The multilayers 104, 210, and 211 are thick enough to also cover the sides of the nanopillar 102, such that the entire nanopillar 102 is covered.

In FIG. 2A, cover/protect layer 205 (which may be the same as the layer 105 in FIG. 1) is then applied to the top of layer 211 and the top of the nanopillar 102. Layer 205 is an electrically insulating film, like silicon dioxide. Layer 205 will protect the top surface of layers 104, 210, and 211 and the nanopillar 102.

Layer 103 will protect the bottom of the substrate 101. Layers 103 and 205 will be the etch mask to form the window 106 shown in FIG. 2B. The backside window 106 inside the substrate 101 ends at layer 104. In FIG. 2B, layer 205 has been removed.

In FIG. 2C, following the processes in FIG. 1, the nanometer pore 208 is fabricated (which includes multilayers 104, 210, and 211) by removing the nanopillar 102. The nanopillar 102 can be removed from the multilayers 104, 210, and 211 by selective wet or dry etching methods. For example, tetramethylammonium hydroxide (TMAH) can etch away the silicon nanopillar 102 from the multilayers 104, 210, and 211.

Figure 3A:
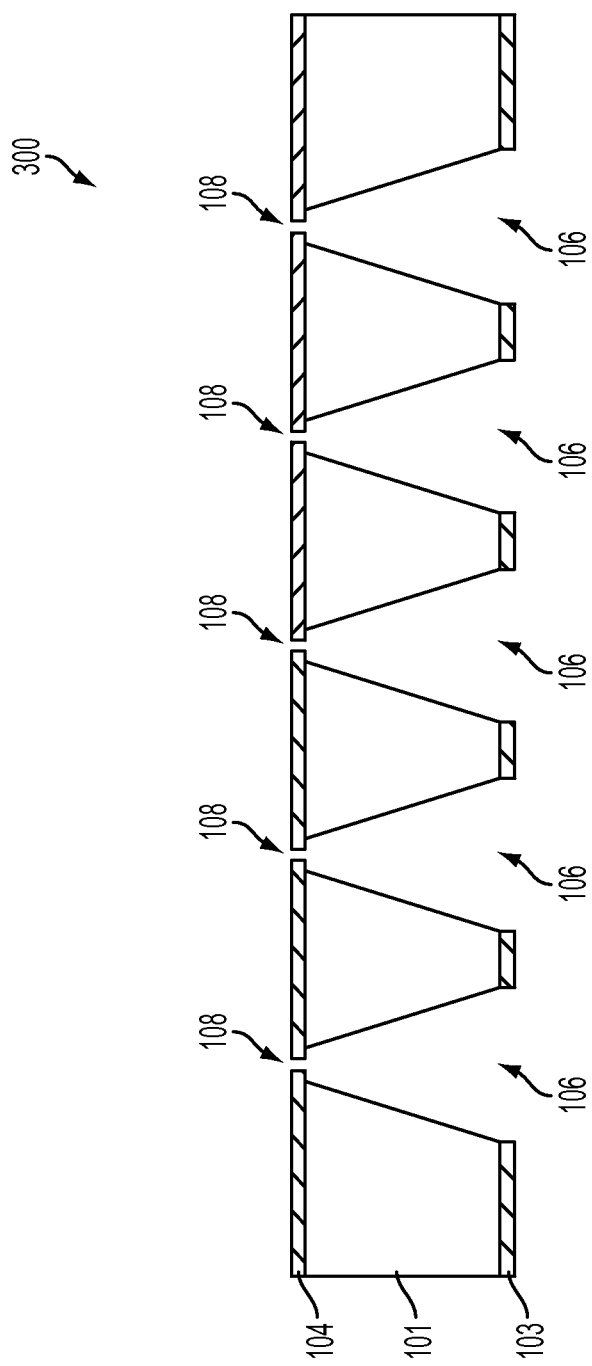
FIG. 3A illustrates a cross-sectional view of a structure for a nanometer pore array of nanometer pores according to an embodiment.
Figure 3B:
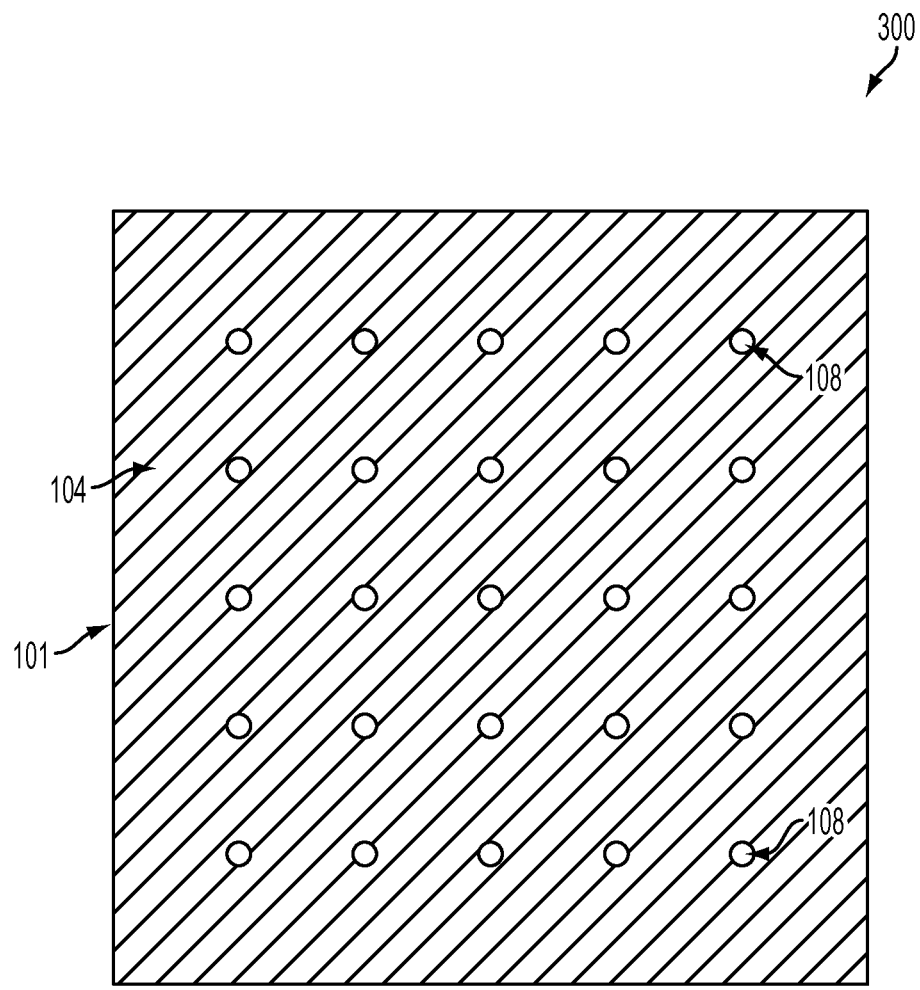
FIG. 3B illustrates a top view of the structure for the nanometer pore array of nanometer pores according to an embodiment.

FIGS. 3A and 3B illustrate the structure for a nanopore array 300 of nanometer pores 108/208 according to an embodiment. FIGS. 3A and 3B are created by the processes disclosed in FIG. 1 but the processes of FIG. 1 are used (simultaneously) to produce an array of nanopores 108 (or nanopores 208). The combination of the processes discussed in FIGS. 1 and 2 are also utilized to produce a multilayer nanopore array of nanopores 208 (like the nanopore array 300) which would then include additional layers 210 and 211 as understood by one skilled in the art based on the teachings as discussed herein.

FIG. 3A depicts a cross-sectional view of the nanopore array 300. The substrate 101 is any electrically insulating substrate. Layers 103 and 104 can be any electrically insulating film. Layer 103 may be utilized as the mask to etch the array of backside windows 106 for substrate 101. Following the processes in FIG. 1, the array of nanopores 108 can be fabricated in the layer 104.

FIG. 3B shows the top view of the nanopore array 300. As can be seen, there are multiple nanometer pores 108 formed though the layer 104 on the substrate 101 using the processes discussed in FIG. 1. Also, note that the top view of the multilayer nanopore array would be similar to FIG. 3B except the viewable top layer would be layer 211.

According to an embodiment, FIGS. 4A, 4B, 4C, 4D, and 4E illustrate a structure depicting the processes to localize a single carbon nanotube and/or multiple carbon nanotubes inside a nanometer pore for DNA sequencing. FIGS. 4A, 4B, 4C, 4D, and 4E may collectively be referred to as FIG. 4.

Figure 4A:
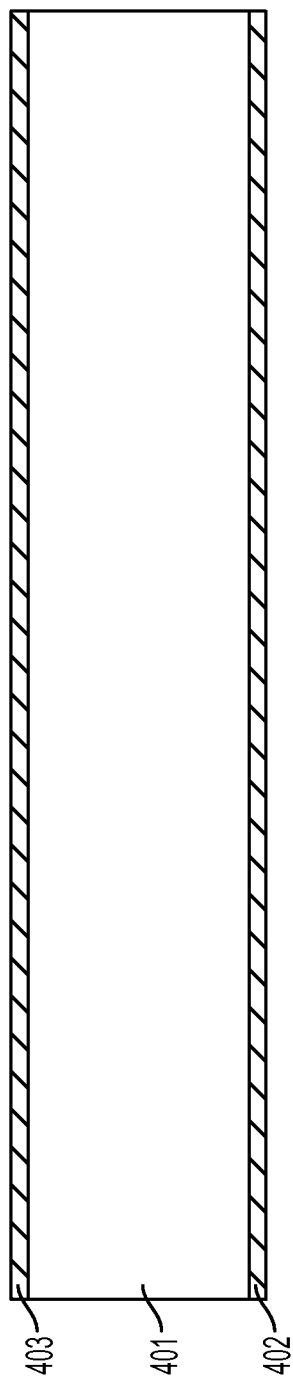
FIG. 4A illustrates a structure depicting the processes to localize a single carbon nanotube and/or multiple carbon nanotubes inside a nanometer pore according to an embodiment.
Figure 4B:
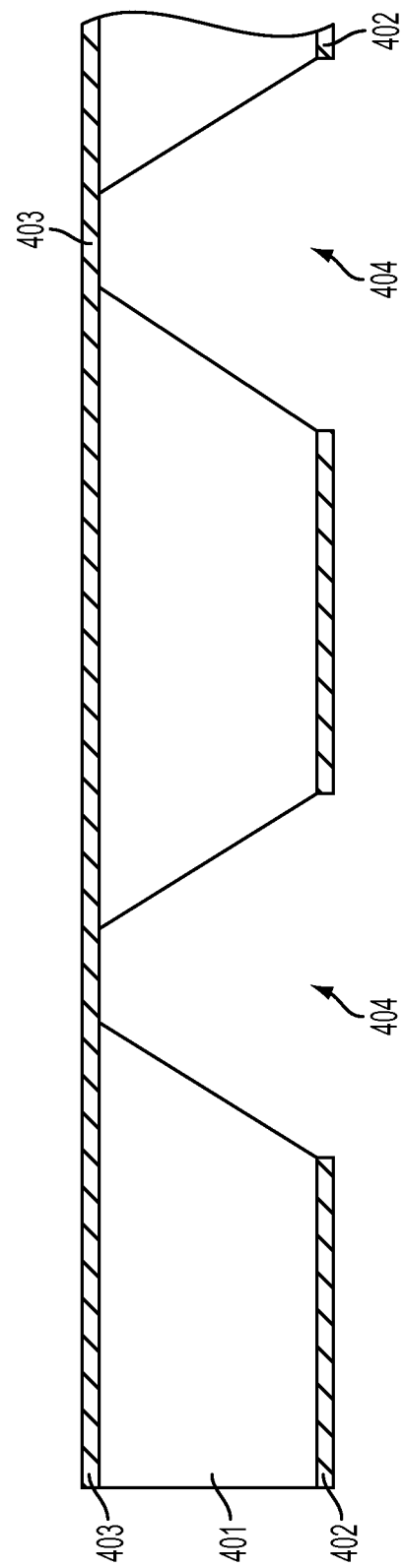
FIG. 4B illustrates the structure depicting the processes to localize a single carbon nanotube and/or multiple carbon nanotubes inside a nanometer pore according to an embodiment.

In FIG. 4A, substrate 401 is any electrically insulating substrate (such as, e.g., silicon). Layers 402 and 403 are electrically insulating films, such as silicon nitride. Layers 402 and 403 can be different types of film or the same. Layer 403 protects the top surface of substrate 401. Layer 402 protects the bottom surface of the substrate 401. Layers 402 and 403 work as an etch mask to form a backside window 404 shown in FIG. 4B. Window 404 can be fabricated by standard semiconductor processes.

Figure 4C:
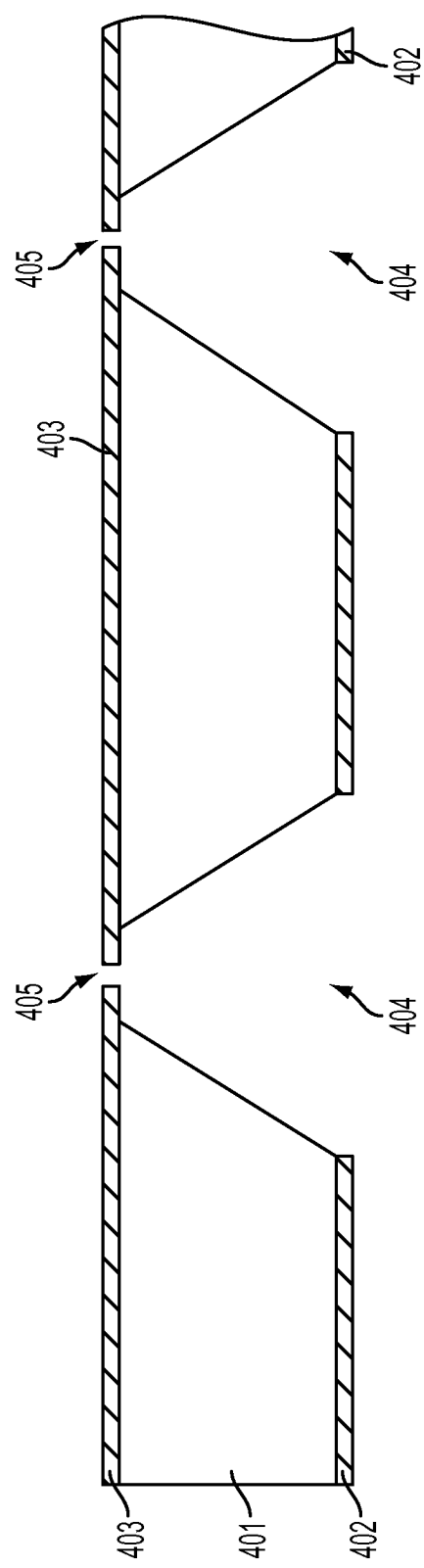
FIG. 4C illustrates the structure depicting the processes to localize a single carbon nanotube and/or multiple carbon nanotubes inside a nanometer pore according to an embodiment.
Figure 4D:
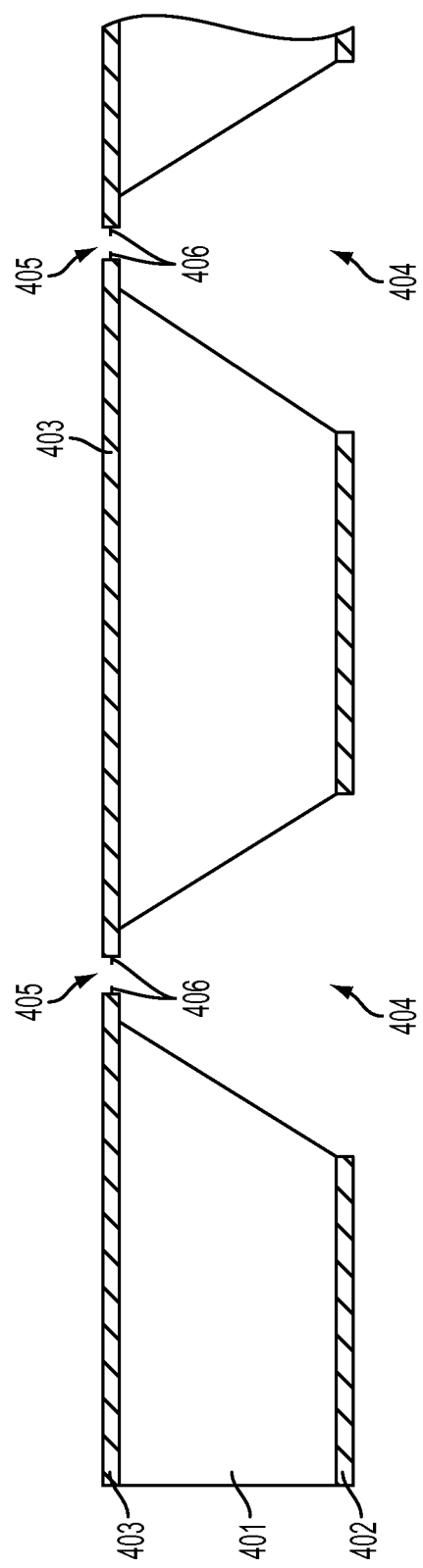
FIG. 4D illustrates the structure depicting the processes to localize a single carbon nanotube and/or multiple carbon nanotubes inside a nanometer pore according to an embodiment.

In FIG. 4C, hole/pore 405 can be fabricated by focused ion beam and/or by electron beam lithography with dry or wet etch processes. The pore 405 can be a nanometer pore from about 10 to about 100 nm. A coating 406 is applied to the inside of the pore 405 as seen in FIG. 4D. The coating 406 is any kind of molecular chemical where one end of which can attach to the inside surface of pore 405, and the other end can capture a single carbon nanotube 480 (shown in FIG. 4E) and/or other nanopillars, like silicon nanopillars. An example of the coating 406 is streptavidin. In one case, the coating 405 (which may be streptavidin), can modified so that the coating 405 can covalently or non-covalently bind to the nanopore surface 405 which has pretreatment with oxygen plasma.

Figure 4E:
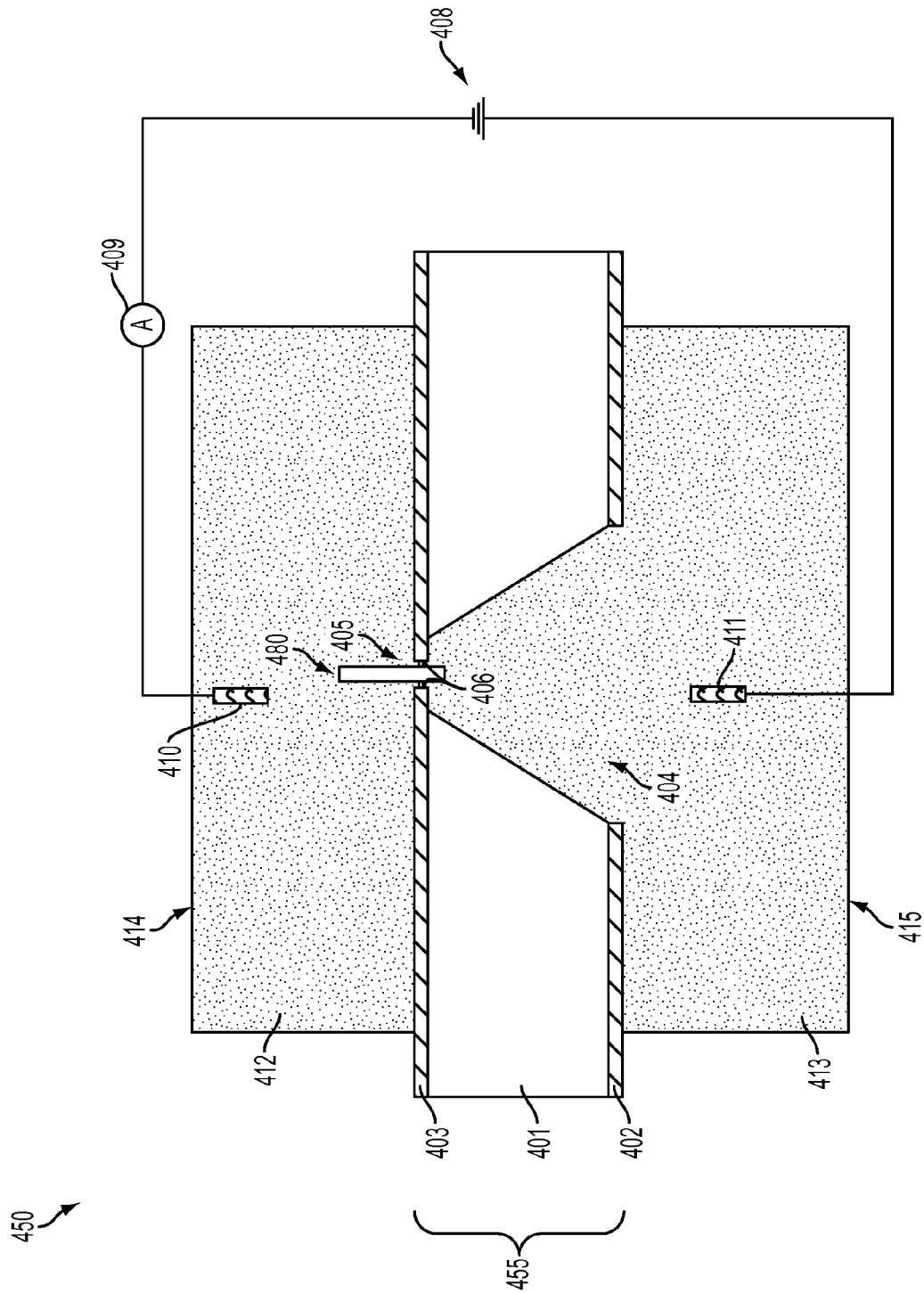
FIG. 4E illustrates a device setup for localizing/positing the carbon nanotube and/or multiple carbon nanotubes inside a nanometer pore according to an embodiment.

In FIG. 4E, a cross-sectional view of device setup 450 is illustrated for positioning the carbon nanotube 480 into the pore 405. Reservoirs 414 and 415 are sealed to opposite sides of a stack 455, and the stack 455 is the structure that includes the substrate 401, layer 402 and layer 403.

The reservoirs 414 and 415 are the reservoirs filled with a solution of electrolytes 412 and 413. The electrolytes 412 and 413 can be potassium chloride. Also, the electrolytes can be ions of $Na^+$, $K^+$, $Ca^{2+}$, $Mg^{2+}$, $Cl^-$, $HPO_4^{2-}$, and/or $HCO_3^-$. An amount of carbon nanotubes (such as the carbon nanotube 480) are put into the electrolyte 412. The amount of carbon nanotubes 480 may correspond to the amount of pores 405 when multiple pores 405 are being processed at once to make an array of nanopores 508 (in FIG. 5) as discussed further herein. Electrodes 410 and 411 are respectively in electrolytes 412 and 413 of reservoirs 414 and 415. The electrodes 410 and 411 are connected by wire to a voltage source 408 and an ampere meter 409. The electrodes 410 and 411 can be silver, silver chloride, or other electrically conducting materials.

The carbon nanotube 480 can be pulled into the pore 405 by an electrical force applied by the voltage source 408. As such, the diameter of the carbon nanotube 480 is smaller than the diameter of the hole/pore 405. The coating 406 can capture and hold the single carbon nanotube 480 inside pore 405. The diameter of carbon nanotube 480 determines the size of nanopore 405. In one case, the diameter of the carbon nanotube 480 may be from 1.0 to 10 nm. The length of carbon nanotube 480 may be from 10 to 200 nm (or even micrometers), which controls the thickness of pore 405. During this capturing process, the ampere meter 409 measures current through the electrolytes 412 and 413. For example, the current measured by the ampere meter 409 changes to indicate the movement of carbon nanotube 480 in the reservoir 414. The current will become less when the carbon nanotube 480 goes inside pore 405. The current will stay at a certain lower current value (that is less then the higher current value measured when the carbon nanotube 480 is not in the pore 405) when coating 406 captures and holds the carbon nanotube 480 in the pore 405. The carbon nanotube 480 can be coated with biotin to help hold/fix the carbon nanotube 480 in the pore 405. The coating of biotin is not shown on the carbon nanotube 480 so as not obscure the figure. Streptavidin is a tetrameric protein which binds very tightly to the small molecule, biotin. The binding constant for this interaction is very high. As such, the coating 406 of, e.g., streptavidin binds to the coating of biotin on the carbon nanotube 480, to tightly bind the carbon nanotube 480 to the pore 405. Based on the teachings disclosed herein, it should be understood that the user can choose any antibody-antigen combinations. The antibody (e.g., coating 406) can bind to the nanopore 405, and the antigen (e.g., coating on the carbon nanotube) can attach to carbon nanotube 480. As one example, the antibody-antigen combination may be for antibody IgG (Immunoglobulin G) and antigen anti-IgG. Additionally, other techniques can be applied to immobilize the carbon nanotube 480 inside nanopore 405. For example, the carbon nanotube 480 can be functionalized with the thiol group (such as, e.g., $—(COOCH_2CH_2SH)$). The carbon nanotube 480 will attach to nanopore 405 through the thiol group when the carbon nanotube 480 enters the nanopore 405 to form the carbon nanotube ($—(COOCH_2CH_2SH)$) nanopore.

Figure 5A:
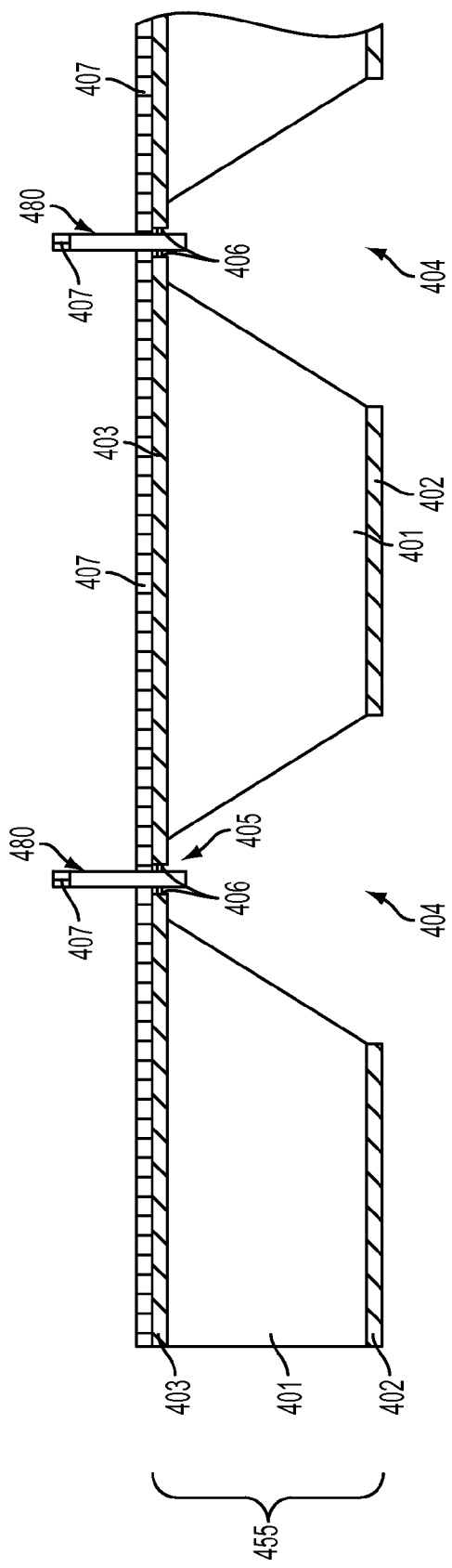
FIG. 5A further illustrates the processes to fabricate the structure for a single nanopore and/or a nanopore array according to an embodiment.

In addition to the processes discussed in FIG. 4, FIGS. 5A, 5B, 5C, and 5D (collectively referred to as FIG. 5) further illustrate the processes to fabricate a structure for a single nanopore and a nanopore array according to an embodiment. In FIG. 5A, the solution of electrolytes 112 and 113 is removed, and the device setup 455 is removed. Now, the localized carbon nanotube 480 is fixed inside the pore 405, and layer 407 is formed on top of layer 403 and on top of the localized carbon nanotube 480. The layer 407 can be insulating or conductive film, like silicon nitride, silicon dioxide, and/or titanium nitride.

Figure 5B:
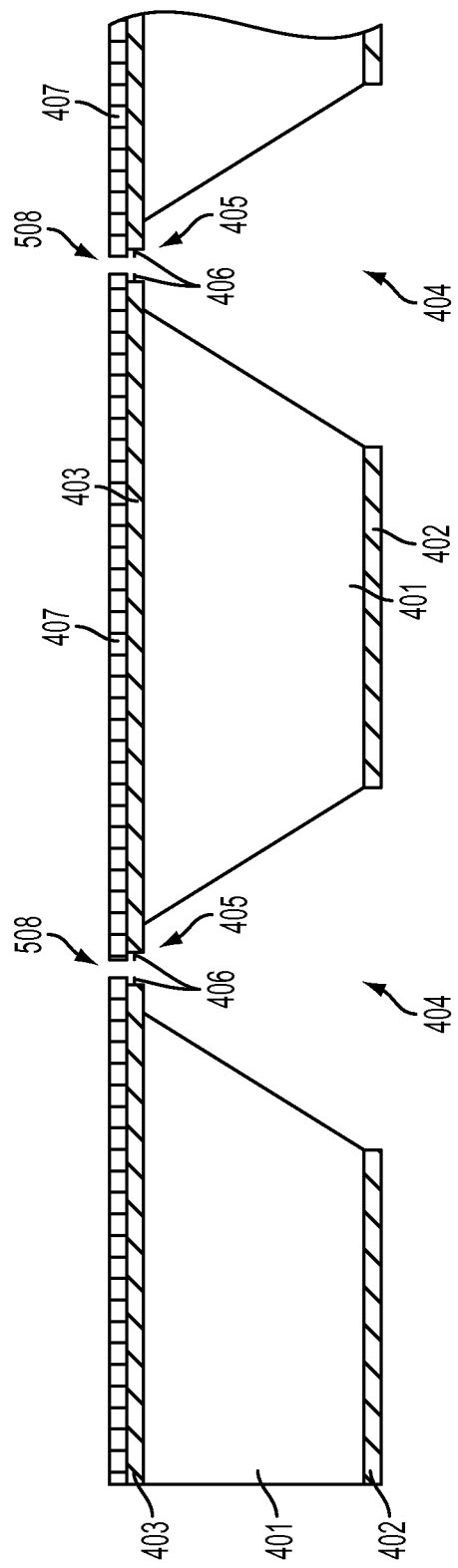
FIG. 5B further illustrates the processes to fabricate the structure for a single nanopore and/or a nanopore array according to an embodiment.

FIG. 5B illustrates how to form nanopore 508 by removing the carbon nanotube 480. FIG. 5B shows a cross-sectional view of the structure with the self-formed nanopore 508. Although two nanopores 508 are shown so as not to obscure the figure, it is understood that numerous nanopores 508 may be fabricated as discussed herein and shown in FIG. 5B. The carbon nanotube 480 can be removed by selective dry or wet etch processes as discussed herein, and understood by one skilled in the art. For example, ozone plasma can be used to efficiently etch away the carbon nanotube 480.

Note that the processes discussed in FIGS. 4 and 5 were utilized to form the nanopore 508 but also apply to forming an array of nanopores 508. The processes in FIGS. 4 and 5 are utilized with numerous pores 405 with their respective coatings 406 to individually attach to respective carbon nanotubes 480. For example, the device setup 450 can have numerous carbon nanotubes 480 in the electrolytes 412 that are to be driven in the open pores 405 in the stack 455. When the voltage source 408 is applied, each individual carbon nanotube 480 is driven into one of the pores 405 and each of the carbon nanotubes 480 is attached in one of the pores 405. The current measured by the ampere meter 409 continues to drop as each individual carbon nanotube 480 attaches to its pore 405. Due to the electrophoretic force applied from the potential of the voltage source 408, the numerous carbon nanotubes 480 are each driven into the nanopore 405. As understood by one skilled in the art, electrophoresis is the motion of dispersed particles relative to the fluid (e.g., solution of electrolytes 412 and 413) under the influence of a spatially uniform electric field (e.g., by the voltage source 408), which drives the carbon nanotubes 480 into respective nanopores 405.

In one case, the coating 406 may be different inside each of the pores 405, and the complementary coating on each of the individual carbon nanotubes 480 is different. Having multiple pairs of coatings for the pores 405 and carbon nanotubes 480 facilitates the capture of each carbon nanotube 480 in its own correspondingly coated pore 405. Each of the carbon nanotubes 480 is removed by wet or dry etching to leave the array of nanopores 508.

Figure 5C:
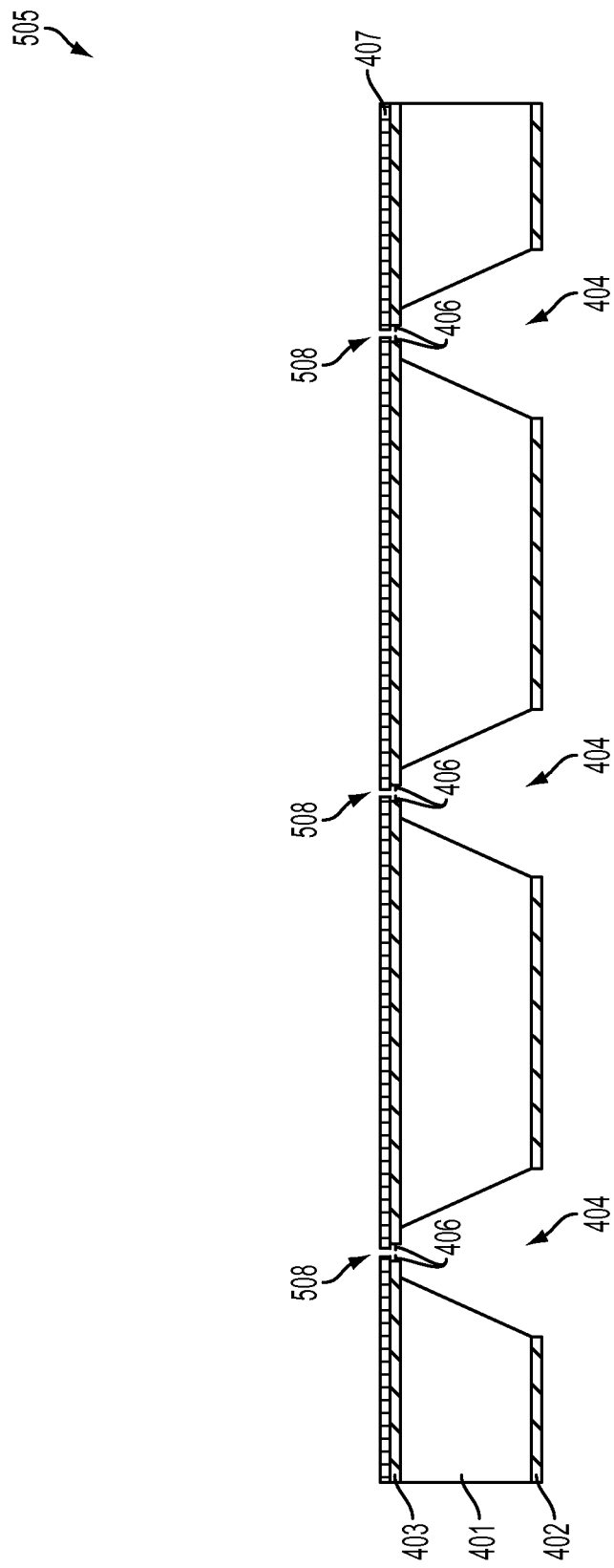
FIG. 5C illustrates a cross-sectional view of a nanopore array according to an embodiment.

As such, FIG. 5C illustrates a cross-sectional view of a nanopore array 505 according to an embodiment. As shown in FIG. 5C, the array of nanopores 508 are each shown in the layer 407 on top of layer 403, substrate 401, and layer 402. Individual windows 404 respectively correspond to individual nanopores 508 in the nanopore array 505. FIG. 5C also shows the respective coating 406 molecules for capturing carbon nanotubes 480.

Figure 5D:
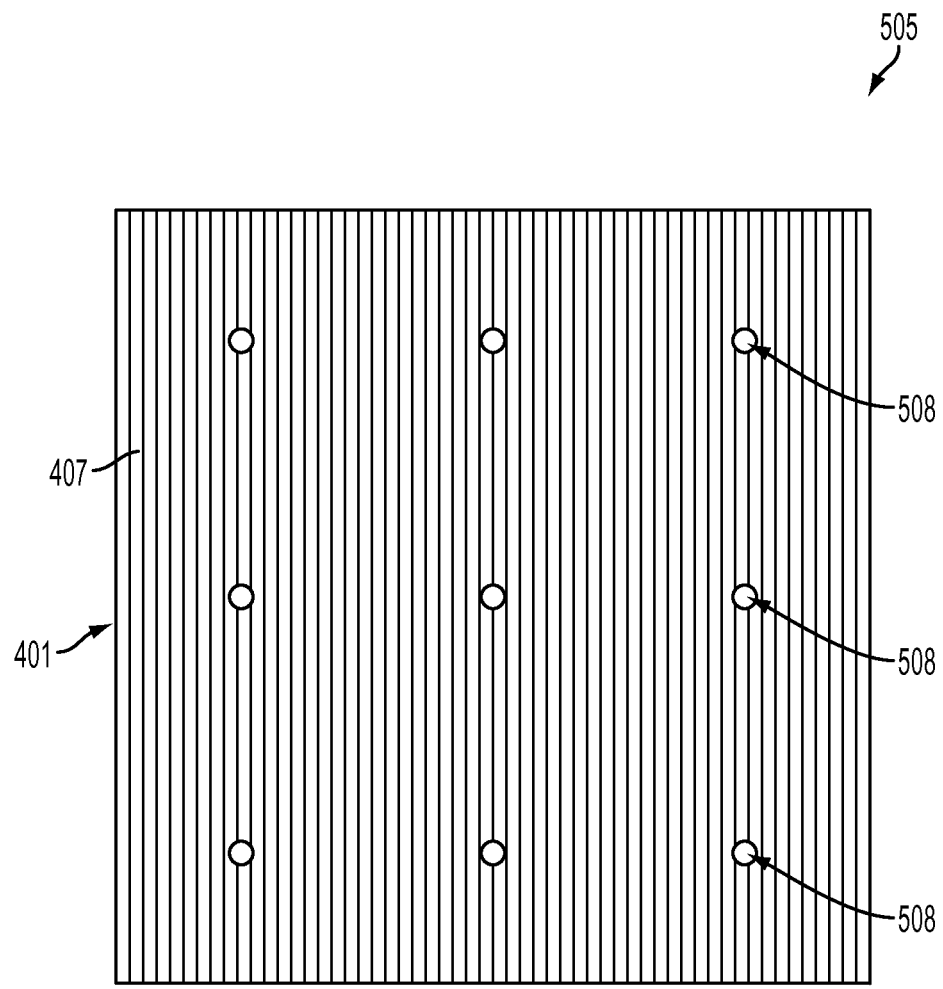
FIG. 5D illustrates a top view of the nanopore array according to an embodiment.

FIG. 5D illustrates a top view of the nanopore array 505 according to an embodiment. As can be seen, the individual nanopores 508 are in the layer 407 which is on the substrate 401. Each individual nanopore 508 corresponds to a previous location of one of the earlier captured carbon nanotubes 480.

Figure 6A:
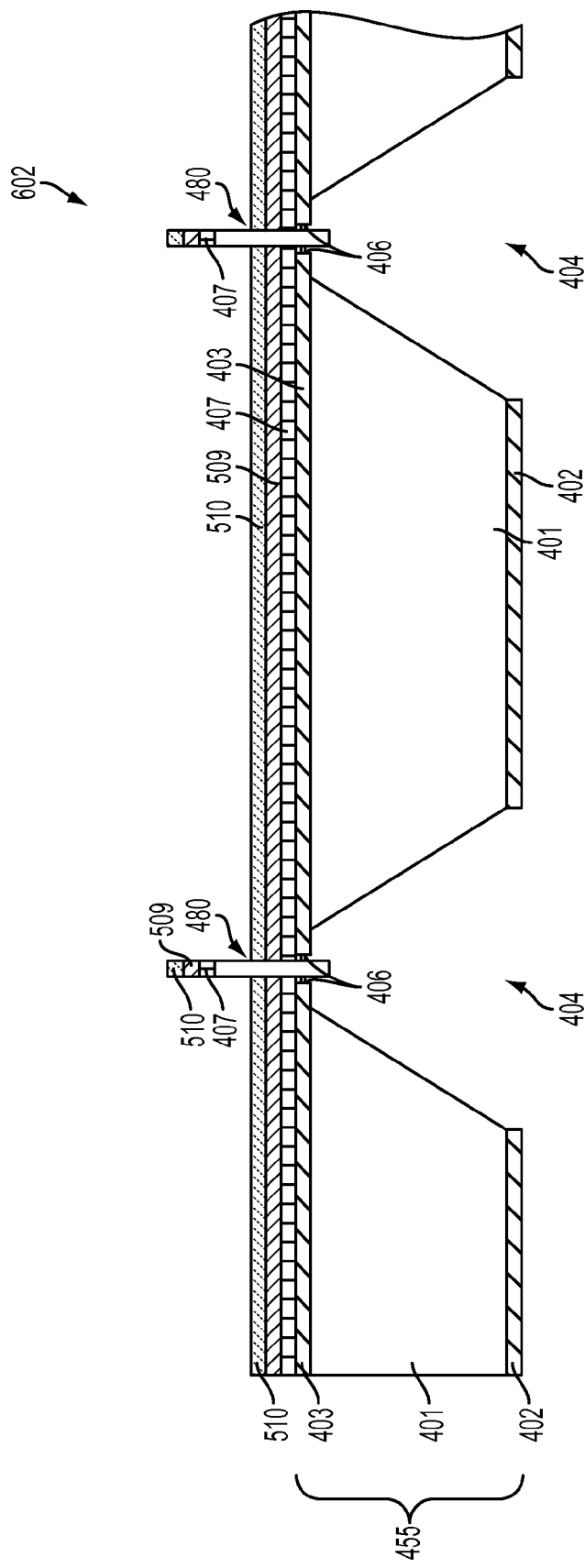
FIG. 6A illustrates the processes to fabricate a nanometer pore through multilayer films of a multilayer structure according to an embodiment.
Figure 6B:
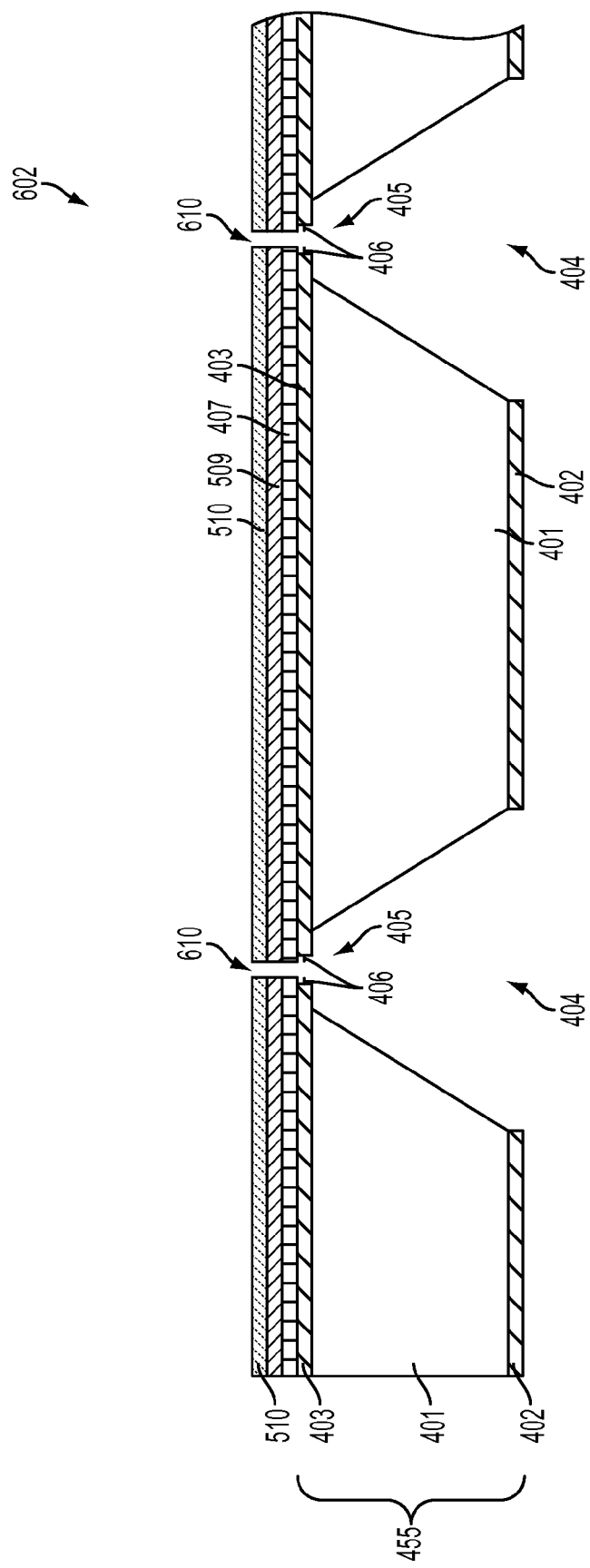
FIG. 6B illustrates the processes to fabricate a nanometer pore through multilayer films of the multilayer structure according to an embodiment.

FIGS. 6A and 6B (collectively referred to as FIG. 6) illustrate a nanometer pore 610 through multilayer films of a multilayer structure 602 according to an embodiment. FIGS. 6A and 6B illustrate a cross-sectional view of the multilayer structure 602. FIG. 6 incorporates processes and discussions provided in FIGS. 4 and 5. Accordingly, FIG. 6 builds on and applies the teaching of FIGS. 4 and 5, and for the sake of brevity, these processes and discussions are not repeated.

FIG. 6A shows the stack 455 which includes the electrically insulating substrate 401, layer 402, and layer 403. The pore 405 is coated with the coating 406 for attaching to the carbon nanotube 480.

As discussed in FIG. 4E, the carbon nanotube 480 is attached to the pore 405 through the coating 406 molecule as shown in the device setup 450. As discussed in FIG. 5A, the layer 407 is applied on top of layer 403 and top of the carbon nanotube 480. Now, with reference to FIG. 6A, layer 509 is applied on top of layer 407 and on top of the carbon nanotube 480. Layer 510 is applied on top of the layer 509 and on top of the carbon nanotube 480. Layers 407, 509, and 510 can be any insulating or conductive film, like silicon nitride, titanium nitride.

In FIG. 6A, the multilayer structure 602 still has the carbon nanotube 480 attached to the pore 405, and the carbon nanotube 480 is through layers 407, 509, and 510.

For the multilayer structure 602, FIG. 6B illustrates the nanopore 610 formed through the layers 407, 509, and 510 after the carbon nanotube 480 has been removed by wet or dry etching processes (e.g., by using ozone plasma to etch away the carbon nanotube.) The teachings of FIG. 6 can be combined with FIGS. 4 and 5 to fabricate a multilayer nanopore array as would be understood by one skilled in the art.

Figure 7:
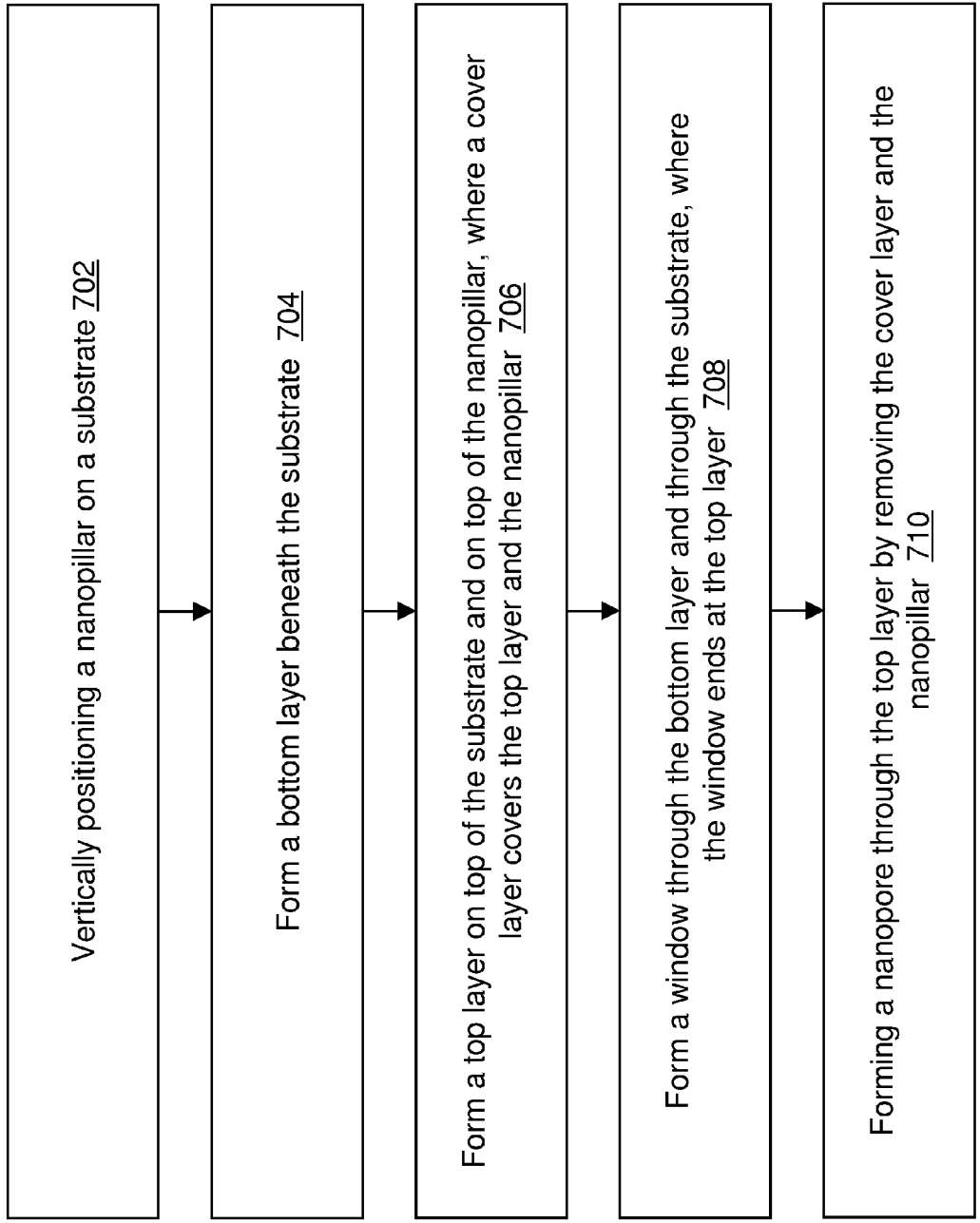
FIG. 7 is a flow chart of a method for configuring a nanopore structure according to an embodiment.

FIG. 7 is a flow chart 700 of a method for configuring a nanopore structure according to an embodiment. Reference can be made to FIGS. 1, 2, and 3.

A nanopillar 102 is vertically positioned on a substrate 101 at block 702. A bottom layer 103 is formed beneath the substrate 101 at block 704. A top layer 104 is formed on top of the substrate 101 and on top of the nanopillar 102, and a cover layer 105 covers the top layer 104 and the nanopillar 102 at block 706.

A window 106 is formed through the bottom layer 103 and through the substrate 101, and the window 106 ends at the top layer 104 (e.g., does not go through the top layer 104) and the bottom of the nanopillar 102 at block 708. A nanopore 108 is formed through the top layer 104 by removing the cover layer 105 and the nanopillar 102 at block 710.

Further, an array of nanopores 108 (as shown in FIGS. 3A and 3B) is formed through the top layer by using multiple nanopillars 102. For example, the array of nanopores 108 are formed by (1) vertically positioning the multiple nanopillars 102 on the substrate 101 (as shown in FIG. 1A); (2) the top layer 104 being formed on top of the substrate 101 and the multiple nanopillars 102 in which the cover layer 105 covers the top layer 104 and the nanopillars 102 (as shown in FIG. 1C); (3) multiple windows 106 being formed through the bottom layer 103 and formed through the substrate 101 in which the multiple windows 106 respectively correspond on a one to one basis to the multiple nanopillars 102 (as shown in FIGS. 1D and 1E); and (4) removing each of the multiple nanopillars 102 and the cover layer 105, where the array of nanopores 108 remain in the top layer 104 at each previous location of the multiple nanopillars 102.

The substrate 101 may be silicon, and the nanopillar 102 may be silicon, silicon dioxide, and/or a carbon nanotube. The diameter of the nanopore 108 formed through the top layer 104 corresponds to (or is the same size as) the diameter of the nanopillar 102. The depth of the nanopore 108 corresponds to (or is the same depth as) the thickness of the top layer 104.

Figure 8:
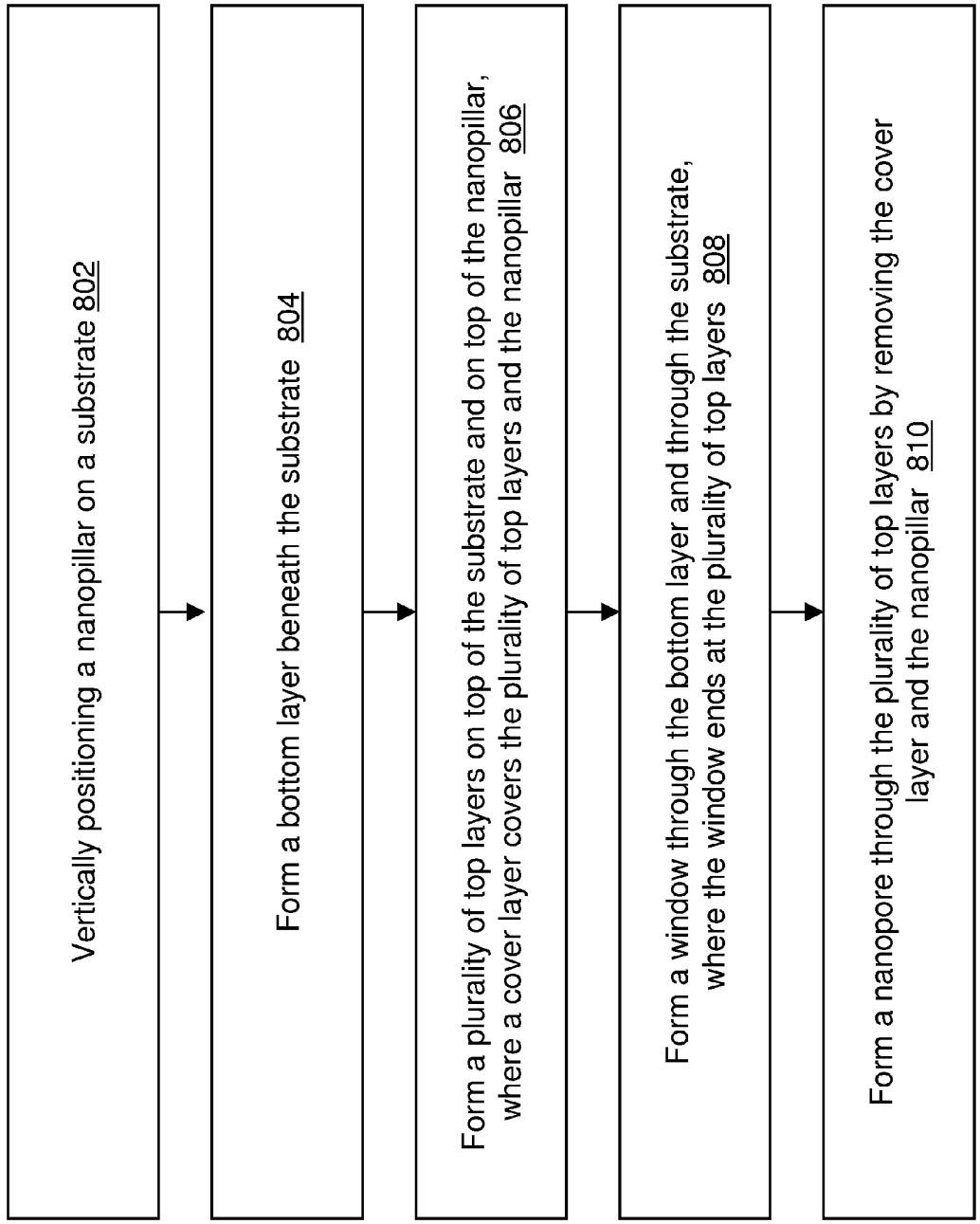
FIG. 8 is a flow chart of a method for configuring a multilayer nanopore structure according to an embodiment.

FIG. 8 is a flow chart 800 of a method for configuring a multilayer nanopore structure according to an embodiment. Reference can be made to FIGS. 1, 2, and 3.

The nanopillar 102 is vertically positioned on the substrate 101 at block 802. The bottom layer 103 is formed beneath the substrate 101 at block 804. Multiple top layers 104, 210, 211 are formed on top of the substrate 101 and on top of the nanopillar 102, and the cover layer 205 (like cover layer 105) covers the multiple top layers 104, 210, 211 and the nanopillar 102 (as shown in FIG. 2A) at block 806.

A window 106 is formed through the bottom layer 103 and through the substrate 101, and the window 106 ends at the multiple top layers (e.g., ends at top layer 104 without going through the top layer 104) and at the bottom of the nanopillar 102 as shown in FIG. 2B at block 808. The nanopore 208 is formed through the multiple top layers 104, 210, 211 by removing the cover layer 105 and the nanopillar 102 at block 810.

An array of nanopores 208 (similar to FIGS. 3A and 3B) is formed through the multiple top layers 104, 210, 211 by using multiple nanopillars 102. The array of nanopores 208 are formed by (1) vertically positioning the nanopillars 102 on the substrate; (2) the multiple top layers 104, 210, 211 being formed on top of both the substrate 101 and the multiple nanopillars 102 in which the cover layer 205 covers the multiple top layers 104, 210, 211 and the nanopillars 102; (3) multiple windows 106 formed through the bottom layer 103 and formed through the substrate 101 in which the windows 106 respectively correspond on a one to one basis to the multiple nanopillars 102; and (4) removing each of the nanopillars 102 and the cover layer 205, such that the array of nanopores 208 remain in the multiple top layers 104, 210, 211 at each previous location of the of nanopillars 102 (similar to FIGS. 3A and 3B).

The substrate is silicon, and the nanopillar 102 can be silicon, silicon dioxide, and/or a carbon nanotube. The diameter of the nanopore 208 formed through the multiple top layers 104, 210, 211 corresponds to the diameter of each respective one the multiple nanopillar 102. The depth of the nanopore 208 corresponds to a combined thickness (i.e., depth) of the multiple top layers 104, 210, 211.

Figure 9:
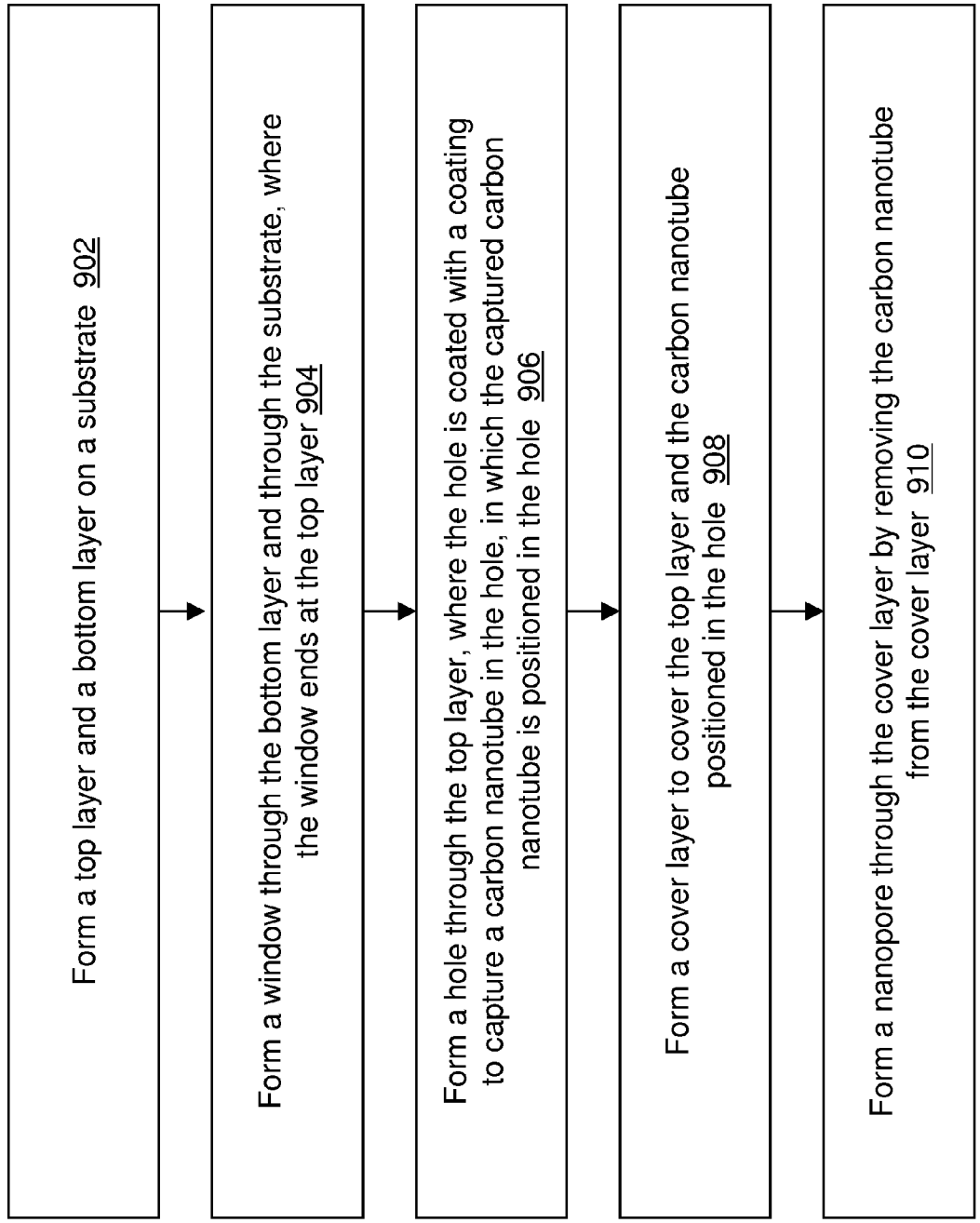
FIG. 9 is a flow chart of a method for configuring a nanopore structure according to an embodiment.

FIG. 9 is a flow chart 900 of a method for configuring a nanopore structure according to an embodiment. Reference can be made to FIGS. 4, 5, and 6.

A top layer 403 and a bottom layer 402 are formed on a substrate 401 at block 902. A window 404 is formed through the bottom layer 402 and through the substrate 401, in which the window 404 ends at the top layer 403 at block 904.

A hole/pore 405 is formed through the top layer 403, and the hole 405 is coated with the coating 406 to capture the carbon nanotube 480 in the hole 405, in which the captured carbon nanotube 480 is positioned in the hole 405 at block 906.

A cover layer 407 is formed to cover both the top layer 403 and the carbon nanotube 480 positioned in the hole 405 at block 908. A nanopore 508 is formed through the cover layer 407 by removing the carbon nanotube 480 from the cover layer 407 at block 910.

An array of nanopores 508 are formed through the cover layer 407 by multiple carbon nanotubes (as shown in FIGS. 5C and 5D). The array of nanopores 508 are formed by: (1) multiple windows 404 formed through the bottom layer 402 and through the substrate 401 in which the windows 404 are to respectively correspond on a one to one basis to the multiple carbon nanotubes 480; (2) multiple holes 405 coated with the coating 406 to respectively capture the carbon nanotubes 480 in the holes 405; (3) the cover layer 407 being formed on top of the top layer 403 and the multiple carbon nanotubes 480 in which the cover layer 407 covers the top layer 403 and the multiple carbon nanotubes 480; and (4) removing each of the multiple carbon nanotubes 480, such that the array of nanopores 508 remain in the cover layer 407 at each previous location of the multiple captured carbon nanotubes 480.

The coating 406 on the inside of the hole 405 is streptavidin, and the coating on the outside of the carbon nanotube is biotin.

Figure 10:
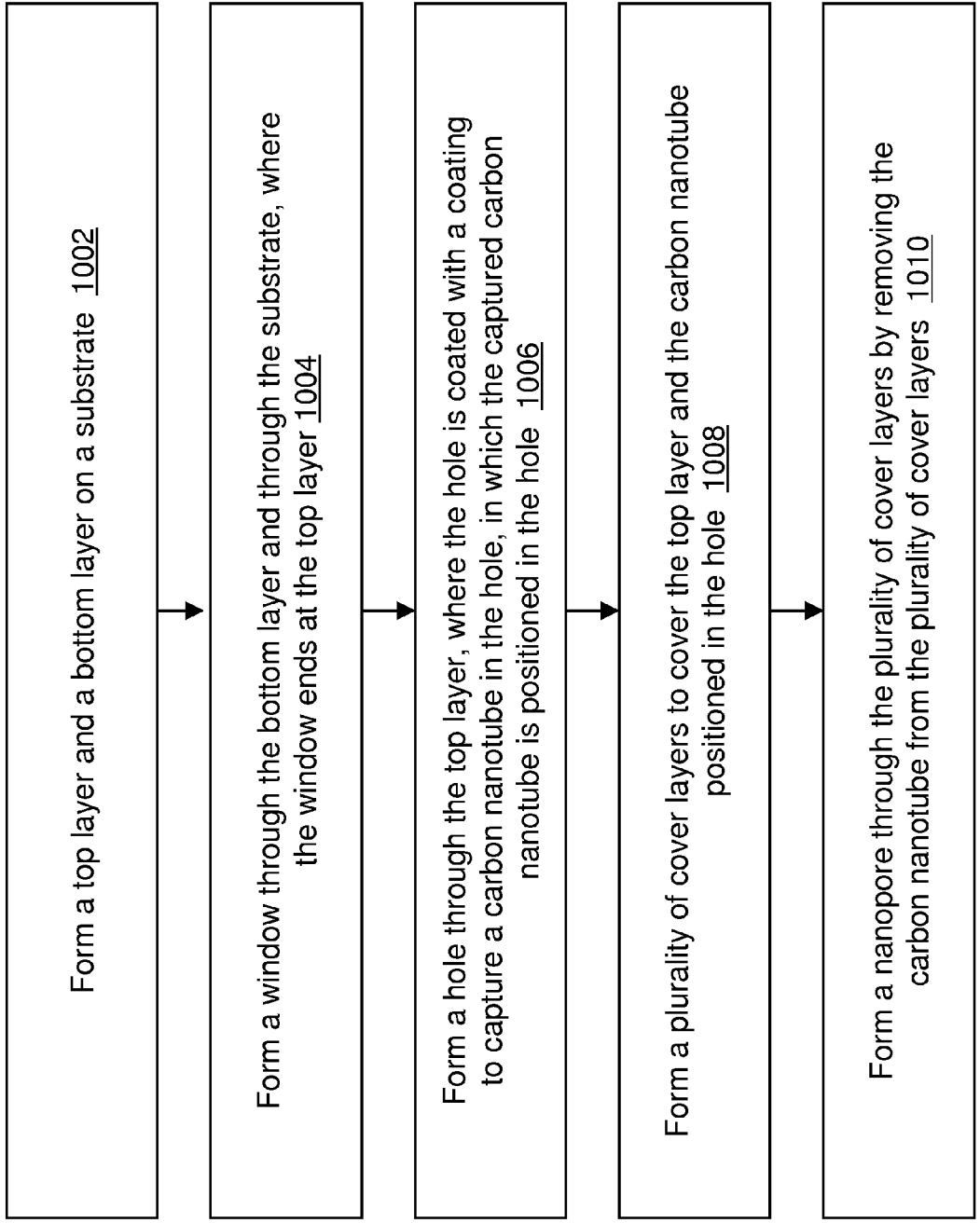
FIG. 10 is a flow chart of a method for configuring a multilayer nanopore structure according to an embodiment.

FIG. 10 is a flow chart 1000 of a method for configuring a multilayer nanopore structure according to an embodiment. Reference can be made to FIGS. 4, 5, and 6.

The top layer 403 and the bottom layer 402 are formed on the substrate 401 at block 1002. A window 404 is formed through the bottom layer 402 and through the substrate 401, and the window 404 ends at the top layer 403 at block 1004.

A hole 405 is formed through the top layer 403, where the hole 405 is coated with the coating 406 to capture the carbon nanotube in the hole, such that the captured carbon nanotube 480 can be positioned in the hole 405 of the top layer 403 at block 1006. Multiple cover layers 407, 509, 510 (e.g., one on top of another) cover the top layer 403 and the carbon nanotube 480 positioned in the hole 405 at block 1008.

A nanopore 610 (similar to nanopore 508 shown in FIG. 5) is formed through the multiple cover layers 407, 509, 510 by removing the carbon nanotube 480 from the multiple cover layers 407, 509, 510 at block 1010.

An array of nanopores 610 (same as for nanopores 508 in FIGS. 5C and 5D) are formed through the multiple cover layers 407, 509, 510 by using multiple carbon nanotubes 480. The array of nanopores 610 are formed by: (1) multiple windows 404 formed through the bottom layer 402 and formed through the substrate 401 in which the windows are to respectively correspond on a one to one basis to the multiple carbon nanotubes 480; (2) multiple holes 405 coated with the coating 406 to respectively capture their own one of the multiple carbon nanotubes 480 in the holes 405; (3) the multiple cover layers 407, 509, 510 being formed on top of the top layer 403 and the multiple carbon nanotubes 480 in which the multiple cover layers 407, 509, 510 cover the top layer 403 and the multiple carbon nanotubes 480; and (4) removing each of the carbon nanotubes 480, such that the array of nanopores 610 (same concept as nanopores 508 except for FIGS. 5C and 5D show a single cover layer 407) remain in the multiple cover layers 407, 509, 510 at each previous location of the multiple carbon nanotubes 480 previously captured.

The diameter of the nanopore 610 formed through the multiple cover layers 407, 509, 510 corresponds to the diameter of the carbon nanotube 480 therein. The depth of the nanopore 610 corresponds to a combined thickness (depth) of the multiple cover layers 407, 509, 510. The coating on the inside of the hole 405 is streptavidin, and the coating on the outside on the carbon nanotube 480 may biotin.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or schematic diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As described above, embodiments can be embodied in the form of computer-implemented processes and apparatuses for practicing those processes. In embodiments, the invention is embodied in computer program code executed by one or more network elements. Embodiments include a computer program product on a computer usable medium with computer program code logic containing instructions embodied in tangible media as an article of manufacture. Exemplary articles of manufacture for computer usable medium may include floppy diskettes, CD-ROMs, hard drives, universal serial bus (USB) flash drives, or any other computer-readable storage medium, wherein, when the computer program code logic is loaded into and executed by a computer, the computer becomes an apparatus for practicing the invention. Embodiments include computer program code logic, for example, whether stored in a storage medium, loaded into and/or executed by a computer, or transmitted over some transmission medium, such as over electrical wiring or cabling, through fiber optics, or via electromagnetic radiation, wherein, when the computer program code logic is loaded into and executed by a computer, the computer becomes an apparatus for practicing the invention. When implemented on a general-purpose microprocessor, the computer program code logic segments configure the microprocessor to create specific logic circuits.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method of forming a structure, the method comprising:
    providing a substrate having a nanopillar vertically positioned on the substrate, wherein a bottom layer is formed beneath the substrate;
    providing a top layer formed on top of the substrate and on top of the nanopillar, wherein a cover layer covers the top layer and the nanopillar;
    forming a window through the bottom layer and through the substrate, wherein the window ends at the top layer; and
    forming a nanopore through the top layer by removing all of the cover layer and the nanopillar, such that none of the cover layer remains on the top layer.

2. The method of claim 1, further comprising an array of nanopores formed through the top layer by a plurality of nanopillars;
    wherein the array of nanopores are formed by:
        the top layer being formed on top of the substrate and the plurality of nanopillars in which the cover layer covers the top layer and the plurality of nanopillars;
        a plurality of windows formed through the bottom layer and formed through the substrate in which the plurality of windows respectively correspond on a one to one basis to the plurality of nanopillars;
        removing each of the plurality of nanopillars and the cover layer, the array of nanopores remain in the top layer at each location of the plurality of nanopillars.

3. The method of claim 1, wherein the substrate is silicon.

4. The method of claim 1, wherein the nanopillar is at least one of silicon, silicon dioxide, and carbon nanotube.

5. The method of claim 1, wherein a diameter of the nanopore formed through the top layer corresponds to a diameter of the nanopillar; and
 wherein a depth of the nanopore corresponds to a thickness of the top layer.

6. A method of forming a structure, the method comprising:
 providing a substrate having a nanopillar vertically positioned on the substrate, wherein a bottom layer formed beneath the substrate;
 providing a plurality of top layers formed on top of the substrate and on top of the nanopillar, wherein a cover layer covers the plurality of top layers and the nanopillar;
 forming a window through the bottom layer and formed through the substrate, wherein the window ends at the plurality of top layers; and
 forming a nanopore through the plurality of top layers by removing all of the cover layer and the nanopillar, such that none of the cover layer remains on the plurality of top layers.

7. The method of claim 6, further comprising an array of nanopores formed through the plurality of top layers by a plurality of nanopillars;
 wherein the array of nanopores are formed by:
  the plurality of top layers being formed on top of the substrate and the plurality of nanopillars in which the cover layer covers the plurality of top layers and the plurality of nanopillars;
  a plurality of windows formed through the bottom layer and formed through the substrate in which the plurality of windows respectively correspond on a one to one basis to the plurality of nanopillars;
  removing each of the plurality of nanopillars and the cover layer, the array of nanopores remain in the plurality of top layers at each location of the plurality of nanopillars.

8. The method of claim 6, wherein the substrate is silicon.

9. The method of claim 6, wherein the nanopillar is at least one of silicon, silicon dioxide, and carbon nanotube.

10. The method of claim 6, wherein a diameter of the nanopore formed through the plurality of top layers corresponds to a diameter of the nanopillar; and
 wherein a depth of the nanopore corresponds to a thickness of the plurality of top layers.

11. A method of forming a structure, the method comprising:
 providing a substrate having a top layer and a bottom layer;
 forming a hole through the top layer, wherein the hole is coated with a coating to capture a carbon nanotube in the hole, the carbon nanotube being captured to be positioned in the hole;
 forming a window through the bottom layer and through the substrate, wherein the window ends at the top layer;
 forming a cover layer that covers the top layer and the carbon nanotube positioned in the hole, wherein the cover layer is not formed in the hole of the top layer; and
 forming a nanopore through the cover layer by removing the carbon nanotube from the cover layer.

12. The method of claim 11, further comprising an array of nanopores formed through the cover layer by a plurality of carbon nanotubes;
 wherein the array of nanopores are formed by:
  a plurality of windows formed through the bottom layer and formed through the substrate in which the plurality of windows are to respectively correspond on a one to one basis to the plurality of carbon nanotubes;
  a plurality of holes coated with the coating to respectively capture the plurality of carbon nanotubes in the plurality of holes, the cover layer being formed on top of the top layer and the plurality of carbon nanotubes in which the cover layer covers the top layer and the plurality of carbon nanotubes;
  removing each of the plurality of carbon nanotubes, the array of nanopores remain in the cover layer at each location of the plurality of carbon nanotubes.

13. The method of claim 11, wherein the substrate is silicon.

14. The method of claim 11, wherein a diameter of the nanopore formed through the cover layer corresponds to a diameter of the carbon nanotube; and
 wherein a depth of the nanopore corresponds to a thickness of the cover layer.

* * * * *